United States Patent [19]
Seale

[11] Patent Number: 5,844,140
[45] Date of Patent: Dec. 1, 1998

[54] ULTRASOUND BEAM ALIGNMENT SERVO

[76] Inventor: Joseph B. Seale, 36 Ledge La., Gorham, Me. 04038-1208

[21] Appl. No.: 703,627

[22] Filed: Aug. 27, 1996

[51] Int. Cl.$^6$ .................................................... G01N 29/26
[52] U.S. Cl. ............................... 73/633; 73/620; 73/621; 310/90.5; 600/437; 600/443; 600/453
[58] Field of Search ................................... 310/90.5, 334; 128/660.1, 660.08, 660.09, 662.06, 660.07, 660.01, 661.01, 661.08, 661.09, 663.01; 364/413.13; 73/602, 620, 625, 626, 633, 641, 642, 643, 621, 634; 600/425, 437, 440, 441, 444, 445, 453, 455, 456, 457, 459, 407

[56] References Cited

U.S. PATENT DOCUMENTS

| | | | |
|---|---|---|---|
| 4,092,867 | 6/1978 | Matzak | 73/609 |
| 4,479,388 | 10/1984 | Matzuk | 73/634 |
| 4,857,781 | 8/1989 | Shih | 310/90.5 |
| 4,936,307 | 6/1990 | Saito et al. | 128/662.06 |
| 5,146,566 | 9/1992 | Hollis, Jr. et al. | 395/275 |
| 5,313,950 | 5/1994 | Ishikawa et al. | 128/662.06 |
| 5,410,232 | 4/1995 | Lee | 318/568.11 |

*Primary Examiner*—Hezron E. Williams
*Assistant Examiner*—Rose M. Miller
*Attorney, Agent, or Firm*—Pierce Atwood; Chris A. Caseiro

[57] ABSTRACT

A servo system for directing the operation of an ultrasound beam is described. The system includes a rotor and stator combination that utilizes electromagnetic forces to move the ultrasound beam in translational and rotational directions. In an embodiment of the invention the rotor is a permanent magnet that may be levitated and moved using a plurality of stator coils. Sensors are used to determine the position of the rotor, which information is used by a controller to regulate the stator operation designed to effect movement of the rotor. The sensors are preferably hall effect sensors. The permanent magnet is optionally placed in a fluid having buoyancy characteristics that reduce the electromagnetic force required to levitate the rotor. The rotor may be located off center within a housing so as to conform to asymmetrical viewing requirements, such as in transcranial Doppler ultrasound measurements.

42 Claims, 14 Drawing Sheets

FIG. 1
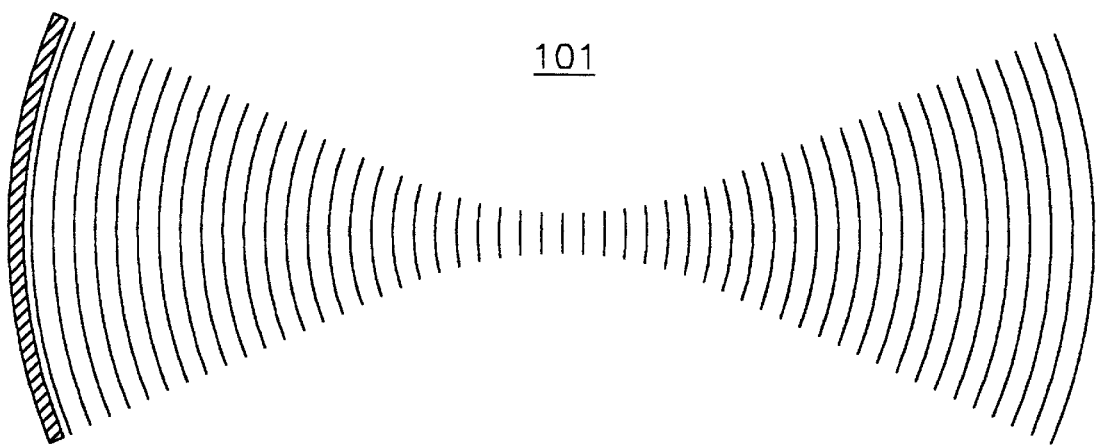
101
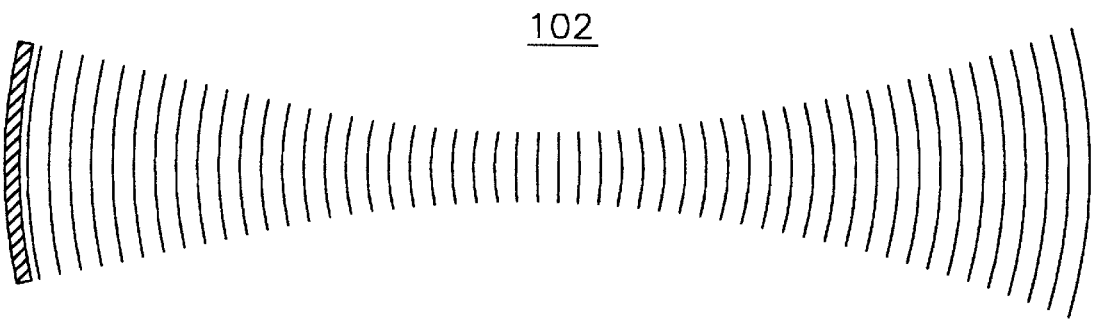
102

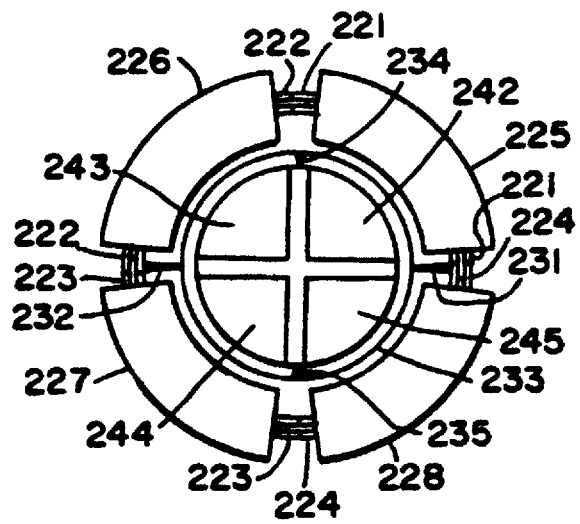
FIG. 2a
FIG. 2b
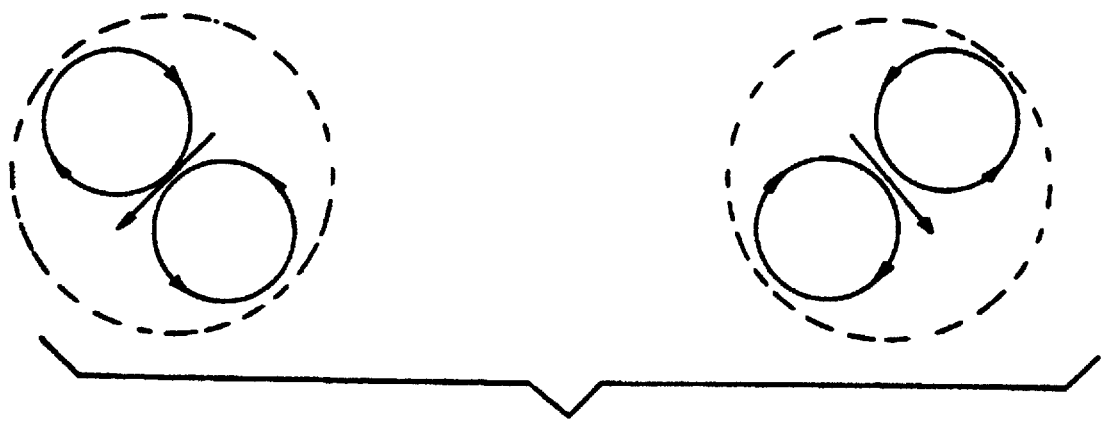
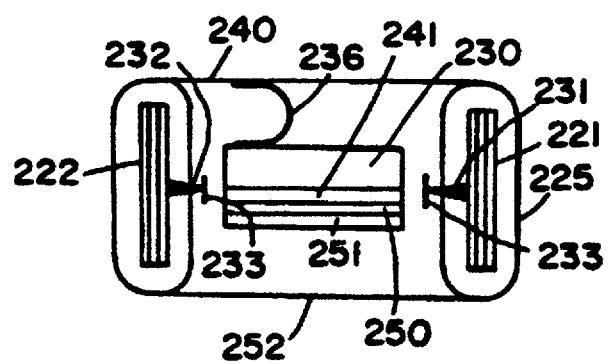
FIG. 2c

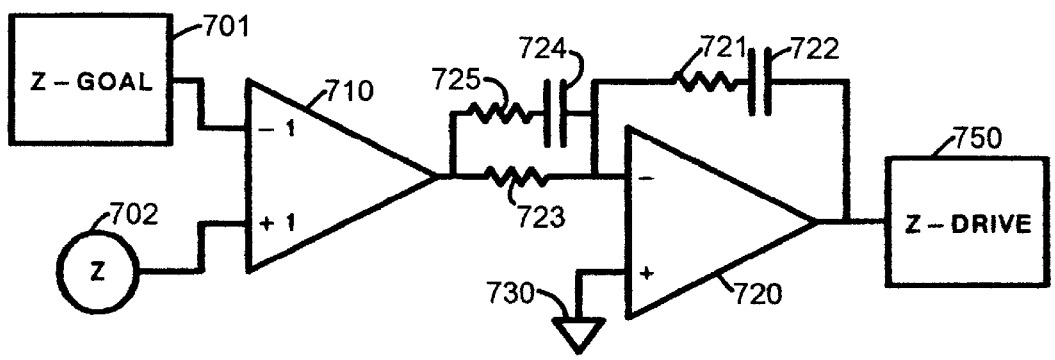
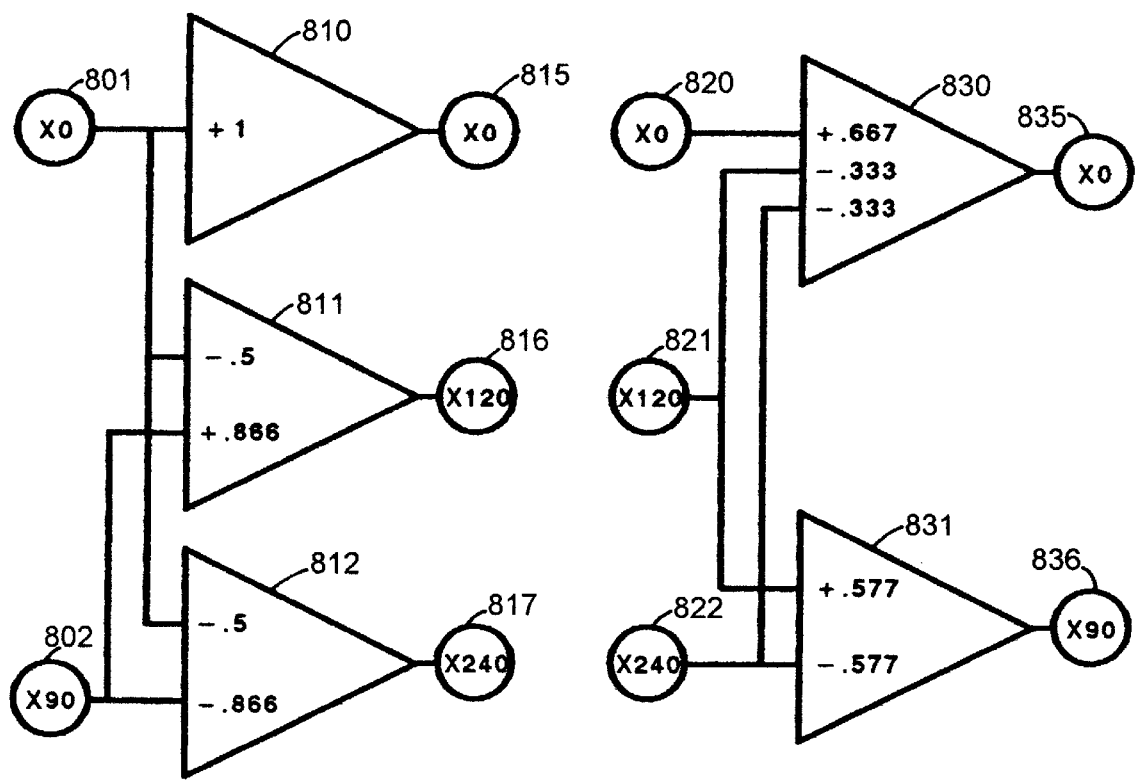

1102 — 1101 — 1102

FIG. 13
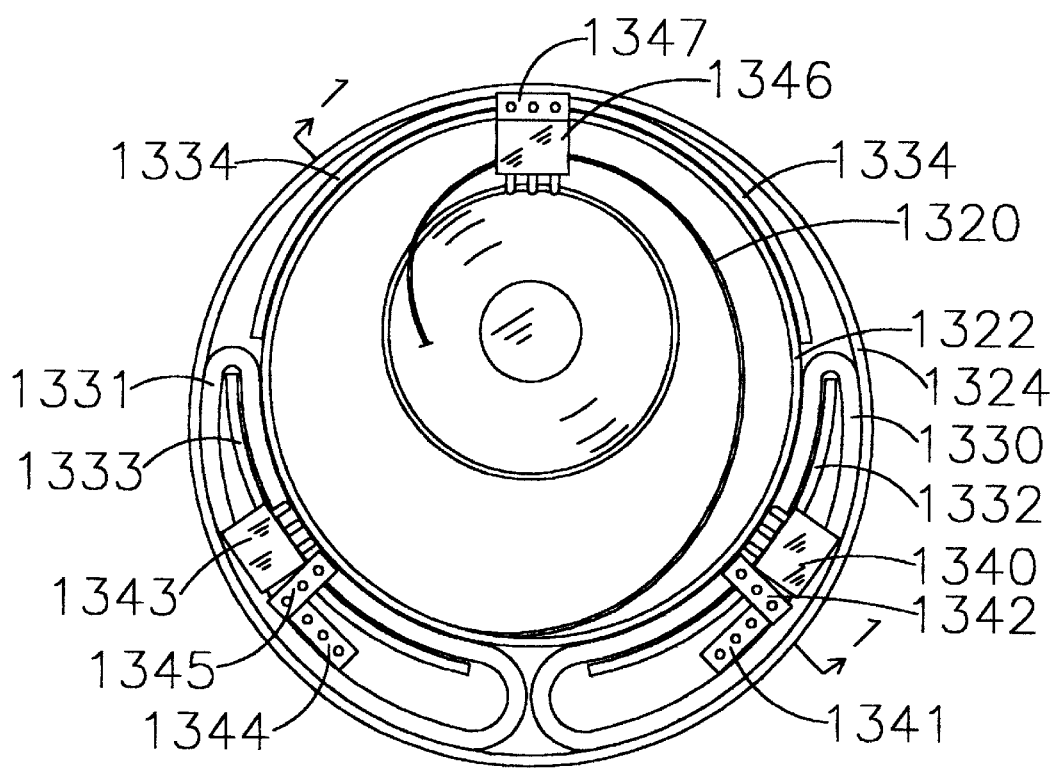
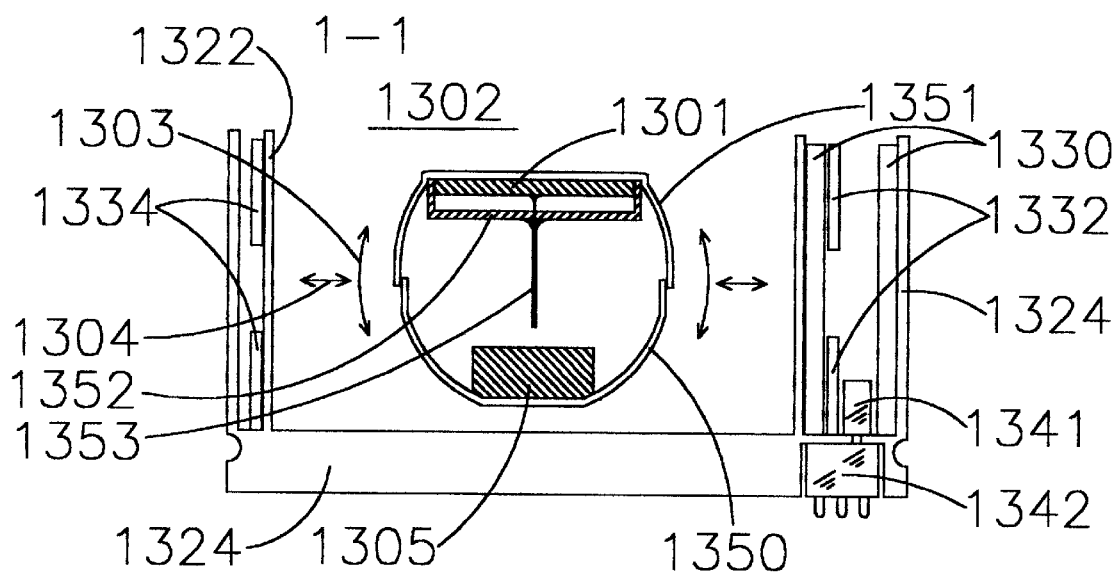

ULTRASOUND BEAM ALIGNMENT SERVO

BACKGROUND OF THE INVENTION

1. Field of the Invention

The present invention relates to devices for controlling the operation of scanning beam systems. More particularly, the present invention relates to devices for regulating the operation of ultrasonic beam transmitters. Still more particularly, the present invention relates to devices for controlling the alignment of an ultrasonic beam in two or more dimensions. The invention has particular application in the field of non-intrusive medical analysis devices but is not limited thereto.

2. Description of the Prior Art.

In the current art, there are no devices in common medical use that control ultrasound beam alignment rapidly and automatically in two dimensions. Devices that scan azimuth angle rapidly while varying elevation angle in small increments have been used experimentally for 3-D image construction, but lack speed in controlling elevation. In the analogous area of laser scanning, it is common to steer a light beam in two dimensions using a pair of orthogonally-rotating mirrors driven by galvanometer movements. The double mirror approach does not work as well with ultrasound, however. The size and cumbersomeness of a pair of galvanometer-driven mirrors is a disadvantage in medical applications, especially for limited-space uses such as transesophageal and transrectal probes. Another design constraint is that the wavelengths of diagnostic ultrasound waves are much larger than optical wavelengths, of necessity, since attenuation of ultrasound waves rises steeply with decreasing wavelength. As a rule of thumb, ultrasound wavelength cannot be much less than 1% of the maximum depth to be imaged, with an even larger wavelength required for imaging through tissues with high attenuation. With relatively large wavelengths, diffraction effects make it impossible to produce very thin collimated beams that can be steered by small mirrors, as with lasers.

For sharp focusing of ultrasound, a relatively large aperture is needed to avoid angular dispersion by diffraction. A well-focused near-field ultrasound beam has the shape of a converging cone connecting to a diverging cone through a short focal neck, representing a small depth of near-optimum focus in 5 the target area: FIG. 1 generally at 101, top. Resolution approaching a practical minimum spot diameter of a little under two wavelengths at the focus demands an included cone angle on the order of 60°. If the originating end of the columnar beam is made smaller while maintaining a fixed focus depth, then diffraction causes the focal neck to become thicker, sacrificing resolution at optimum depth for an increased depth-range of relatively good focus: FIG. 1, generally at 102, bottom. To achieve fine focus with a double mirror apparatus, the mirrors must be comparatively large, increasing the difficulty of attaining fast angular response. The extra ultrasound path length involving the two mirrors also reduces sharpness of focus. In ultrasound scanning for real-time imaging, competitive image quality commonly demands that an angular sector of 60° or more be swept at 20 Hz or more, to capture motions at cardiac rates and give a sense of image continuity. Without a flicker-combatting system that stores ultrasound frames and refreshes the display several times for each frame update, the sweep rate needs to be considerably higher than 20 Hz. Such high scanning frequencies and angles are difficult to achieve electromechanically in a large-aperture device that is also asked to point the beam at fixed angles and move quickly and precisely from angle to angle.

Typical electromechanical ultrasound image scanners employ multiple transducers on a rotating head, or an ultrasound mirror rotationally vibrating at an angular resonance—approaches that achieve desired azimuth scanning by sacrificing the possibility of precise angular servocontrol in a non-scanning mode.

In radar, phased arrays permit rapid scanning and abrupt alignment changes in two dimensions from a fixed transmit/receive surface. While a comparable approach is in principle applicable to medical ultrasound, in practice the demands of miniaturization and economy have held back development. One-dimensional ultrasound phased arrays are finding widespread use, and limited control of alignment in a second dimension is beginning to appear. In experimental work reported by McCann, Sharp, Kinter, McEwan, Barillot, and Greenleaf (Proc. of the IEEE, Vol. 76, No. 9, Sept. 1988), a stepper motor is used to rotate the scanning plane of a one-dimensional phased array through small incremental steps in order to construct a three-dimensional digital image. This approach requires that the target and the ultrasound scanner be mechanically stabilized so that frames of a slow scan are in precise registration. Adaptive alignment tracking of moving cardiac surfaces or rapid spatial referencing to a "fixed" target (a biological "pole star" such as a major bone) cannot be contemplated with such a device. Shaulov, in U.S. Pat. No. 4,671,293, describes a phased array with dual sets of electrodes that permit beam steering in either of two selected scanning planes. Such a device can be used, e.g., to display vertical and horizontal cross-sections of the heart simultaneously, but the device cannot achieve arbitrary beam alignments in two dimensions. In other art, in U.S. Pat. No. 4,103,679, Aronson describes a system that employs a one-dimensional ultrasound array to achieve controllable alignment and focus depth in a plane, for use in range-gated pulsed Doppler to characterize the flow velocity profile over the cross-section of an artery. The device is also useful to quantify angular relationships, through comparing Doppler velocities at different axial locations along an artery, so that the relationship between Doppler frequency shift and flow velocity can be determined accurately. It is noted that in the devices of Aronson and others, where adaptive focusing is achieved in a single plane, focusing in the other alignment plane is fixed or manually variable. This lack of autofocusing in one plane limits the information gathering ability of automated ultrasound analysis systems.

In many emerging ultrasound applications, visual image scanning takes on a supporting role of identifying structures and defining their positions, in preparation for analytic measurements in a small region, as in Aronson's invention (op. cit.), which is concerned with measuring flow velocity profiles over the dimensions of an artery and over time, to characterize volumetric flow and to detect the flow disturbances caused by stenotic lesions. In an invention described by Seale in U.S. Pat. No. 4,646,754 and 4,771,792, using fixed-alignment defocused beams or beams electromechanically aligned with respect to two axes, ultrasound is used to track the time-varying positions of organ surfaces generating specular reflections, for the purposes of vibration tracking and diameter pulsation tracking, in a system to determine blood pressure, intraocular pressure and mechanical tissue properties. These two patents describe a non-focusing 2-axis ultrasound aiming device, FIGS. 2a, 2b, and 2c in this writeup (originally FIGS. 11a, b, and-c in U.S. Pat. No. 4,646,754 and FIGS. 12a, b, and c in U.S. Pat. No. 4,771,792), consisting of an ultrasound transducer disk 241 stacked on a short magnet cylinder 230 and the transducer-magnet pair mounted in a 2-axis gimbal bearing, consisting of pins 231, 232, 234 and 235 engaging bearing cups on ring 233 and magnet 230, with flexible wires 236 and others not shown connecting the gimbaled part to fixed housing 240. Surrounding the gimbal is a torroidal ferromagnetic core in four sections, 221 through 224, with four windings 225 through 228 on the four 90° quadrants of the core. Opposite windings are interconnected, giving two electrical circuits that generate two orthogonal magnetic fields crossing the gimbaled transducer-magnet pair, as illustrated schematically in FIG. 2b. The gimbaled part tilts in response to the two applied fields, aiming the ultrasound beam.

In this aiming device, the axially-poled center magnet is inherently unstable in its center alignment, being attracted to point across the torroid. To stabilize alignment, the torsional restoration of the connecting wires must overcome the magnetic instability. Alignment direction is determined open-loop by the balance of mechanical and magnetic forces, without direct sensing for servo-control. In an uncompensated open-loop control situation, if the net alignment restoration is weak, then settling is slow, and if restoration is made stronger, then the steady power needed to maintain off-center alignments becomes excessive. U.S. Pat. No. 4,646,754 describes a compensated open-loop controller whose action takes into account the known dynamic properties of a particular design, i.e. inertia, angular spring coefficient, damping, and electromagnetic coupling strength, for the purpose of speeding response. The term "pole-zero compensation" is often applied to this kind of a controller, since LaPlace pole-zero analysis is commonly used to design the controller transfer function. To speed responses, the controller transfer function cancels electromechanical low-frequency zeroes with poles and low-frequency poles with zeroes, generally replacing the poles removed with new poles as far to the left of the origin as is practical within bandwidth constraints.

A limitation of this open-loop response compensation approach is that it is only as effective as the accuracy to which transducer dynamic characteristics can be known and reproduced from unit to unit. An approach that generally leads to more precise, speedy response with fast settling is the servo approach, wherein an actual measure of ongoing mechanical response is fed back to the controller and used to generate an error signal, which in turn is used in determining controller output to drive the transducer so that the error is reduced rapidly. In the two patents by Seale cited above, the system described uses closed-loop servo control only in relation to small misalignments relative to an ultrasound target, using phase difference information from the ultrasound transducer to maintain alignment perpendicular to a specular reflector after approximate aim is established. Servo control of absolute direction is lacking.

Something much needed and unavailable in existing designs is fast mechanical alignment capability together with alignment sensing and error feedback for rapid, fast-settling changes in alignment. In areas of alignment tracking and analysis of echo features and their movements or velocities, particularly for extended monitoring in unanesthetized subjects, there is need for a combined ability to scan rapidly for image presentation and to fine-tune two-dimensional beam alignment under continuous software control, to maintain alignment dynamically on a tissue structure subject to extended monitoring.

In the area of combined scanning and fixed-beam-alignment monitoring, Matsuo and Miyajima, in U.S. Pat. No. 4,622,978, describe a phased array device that switches readily between B-Mode image scanning and Doppler tracking at a specified alignment within the image plane. A device like this, with phased-array speed, can alternate between scanning sweeps and brief periods of Doppler data gathering at a fixed alignment in a time-multiplexed mode, achieving relative continuity of both image and Doppler data. Electronic alignment control is restricted to a single axis, while manual control is needed for the second axis. Kawabuchi, in U.S. Pat. No. 4,677,853, describes a dual beam ultrasound device, using one beam for tracking data from a fixed target and the other beam for on-going scanning to aid the operator in maintaining alignment on the desired target. Again, the other axis of alignment is controlled manually.

While ultrasound signal analysis holds potential for extended continuous monitoring of various bodily functions, realization of that potential is held back largely by the lack of a cost-effective technology for rapid automated aiming and alignment tracking of ultrasound beams in two dimensions. Ability to time-multiplex tracking with image-scanning in an arbitrary plane would have obvious advantages. Further, an economic way to combine the functions of depth-focusing and alignment control has been lacking. Where near-optimum lateral resolution is sought, ultrasound aperture must be large and, consequently, depth of field small. A device that approaches resolution limits must provide an appropriately large aperture along with rapid automatic focusing, so that a region of visual or analytic interest is readily brought into fine focus without manual disturbance of transducer alignment, as tends to happen when an operator must adjust a focusing lever directly on the transducer head. While annular array ultrasound transducers generate optimized focus at a prescribed depth and good focus over a depth range by use of dynamic autofocusing during the echo reception period, the array technology lacks the simplicity and economy of single transducer optical focus technology. There has been an unmet need for moderate speed of aligning and focusing combined with great simplicity, economy, and compactness: the underlying technology required to build products in the area of routine continuous monitoring. For example, a fetal heart rate monitor capable of locating, focusing on, and adaptively tracking a mitral valve or ventricular wall would have superior performance to existing devices.

For many applications it is advantageous to achieve a device small enough so that it can be affixed directly to the subject's body and ride body motions, rather than clamping both subject and ultrasound equipment to a bench. The advantages of the present invention in fulfilling these and other needs will be seen in the following specification and claims.

BRIEF SUMMARY OF THE INVENTION

The AimServo system of the present invention aligns an ultrasound beam by controlling an electromagnetically levitated rotor whose motions alter the beam path. Path alterations include path direction alignment in two rotational dimensions, and commonly, translation of the beam path in one or two directions not parallel to the path, typically to view a target through a window, e.g., a heart valve through a space between ribs or a cerebral artery through a thin window in the skull. The system is useful for depth imaging of ultrasound echoes and for Doppler velocity imaging, including with depth resolution, e.g., by range gating. Using two or more ultrasound transducers, at least one of which is under AimServo control, the system is useful for evaluating ultrasound absorption as a function of beam path. When sufficient path variability is provided by one AimServo and multiple fixed transducers or by two or more AimServos, computer tomography algorithms familiar in X-ray CAT scans are adapted to derivation of 3-dimensional ultrasound absorption maps. Adapting the methods of wide baseline interferometry familiar in the context of radio telescopes, the AimServo system can use beam path translation and rotation to image a small target area from a range of base locations, leading to a computational derivation of a high resolution image equivalent to that obtainable from an aperture of dimensions too large for practical achievement with a fixed system of ultrasound lenses and/or reflectors. Adapting techniques from telescope optics, employing curved reflectors and aberration-correcting lensing, the AimServo system can provide 2-dimensional directional alignment and depth focusing with a single one-channel ultrasound transducer.

Distinct from imaging are the tracking modalities, where a time-varying parameter such as flow velocity is to be determined for a small target volume in a situation where target and/or sensor position and orientation vary over time, demanding dynamic correction of the ultrasound beam path. Two notable applications are fetal heart rate monitoring and cerebral blood flow monitoring. In the former application the target, a pulsating heart valve or ventricle wall, shifts position over time as the baby moves, and in both applications the sensor moves on a stretchy skin surface and is easily bumped. Small-perturbation dither of the beam path is used to determine a direction for corrective alignment toward improved signal reception. Scanning for target location can be followed by dynamic tracking of the target, using a single AimServo sensor.

Alternative techniques allow the levitated rotor to alter beam path rotation and translation: the levitated rotor carries either an ultrasound transducer or an ultrasound mirror. Since differing applications favor one or the other technique, embodiments will be shown for both.

Fundamental to the AimServo system is the electromagnetic system for levitating, translating, and rotating the rotor under servo control. Actuation forces arise between a primary field magnet and multiple drive windings, the magnet in the stator or rotor and the windings on the opposite side, in the rotor or stator, respectively in moving magnet or moving coil topologies. Rotor position is determined by sensing a position-dependent magnetic coupling between a beacon field and beacon sensors. The beacon field may be either an AC carrier field or "DC," the fixed dipole moment of the primary field magnet. In the DC case, the beacon field must be sensed on the drive winding side of the system, opposite the primary field magnet. In the AC case, the beacon field may be generated either on the primary field magnet side or on the multiple drive winding side, with sensing of this carrier field taking place on the opposite side. Although the instant invention encompasses the multiple topologies of field magnet opposite drive windings and beacon field opposite beacon sensors, certain topologies have distinct practical advantages to be discussed in this disclosure.

In the case of DC field sensing, hall effect sensors are typically arrayed among the multiple drive windings, and the outputs of these sensors are corrected in proportion to the currents going to the drive windings, so that the detected outputs represent only rotor position and are not affected by the actuation magnetic fields.

In the case of AC field sensing, by far the simplest design methodology is called the system of Beacon Coordinates. In this approach, the beacon field is generated by a beacon coil wound concentric with and aligned to the primary field magnet to give an AC dipole moment substantially congruent with the DC dipole moment of the primary field magnet.

In the beacon coordinate approach, the beacon sensors are either the multiple drive windings themselves, or separate sense windings wound with the drive windings to provide congruence between the drive-to-magnet actuation couplings and the beacon sensor-to-coil couplings. Useful electronic sense signals include the voltage differential generated across a current sense resistor or current sense inductor in series with a drive winding; the output from a current-sense transformer in series with a drive winding; the carrier-frequency component of the voltage measured at the output of a current-output (i.e. high output impedance) amplifier driving a drive winding; and the voltage measured across the leads of a separate sense winding. The position-dependent coil-to-winding couplings of the Beacon Coordinate system are variable mutual inductances. An obvious approach to the measurement of these inductances is synchronous demodulation of the carrier signal components received from the sense windings. The demodulated amplitudes of the multiple detected carrier signals represent rotation and translation coordinates, useful both for mapping of ultrasound beam paths and for closing the servo control loop to scan or move quickly and accurately between prescribed beam paths. As will be discussed in greater detail below, the measured mutual inductances of the beacon coordinate system are directly proportional to the energy-per-ampere fields of the actuation couplings. The spatial gradient components of these energy-per-ampere field coupling are the components of generalized force (linear and torsional) that drive the rotor. A description of these field couplings is therefore a simultaneous description of the geometric position/orientation coordinate mapping and of the position/orientation dependent actuation force couplings.

This patent application will concentrate on the base technology of magnetic levitation of a rotor and servo sensing and control of multiple coordinates of rotor motion, as well as ultrasound system applications of this base levitation technology.

BRIEF DESCRIPTION OF THE DRAWINGS

FIG. 1 illustrates diffraction-limited focusing of an ultrasound beam for large and small apertures;

FIG. 2a illustrates an electromechanical ultrasound beam alignment mechanism from previous art in plan, while FIG. 2b illustrates magnetic fields across the middle of the mechanism, and FIG. 2c illustrates the same mechanism in elevation section;

FIG. 3a illustrates a fixed-focus beam alignment servo for monitoring diameter and flow in a common carotid artery, while

FIG. 5a illustrates details from FIG. 3a, of the fixed-focus ultrasound transducer and spring-wire suspension in center alignment, while

FIG. 7 illustrates the basic servo circuit for nulling the error between a linear or angular position coordinate and an input goal signal.

FIG. 8 illustrates matrixing circuitry for going between control (x,y) coordinates and the 120-degree symmetry coordinates of the three angular drive s of FIG. 5c.

FIG. 11a illustrates straight-ahead focusing at a typical depth, while FIG. 11b illustrates rotor translation away from the ultrasound transducer and resulting focus at a shallower depth, FIG. 11c illustrates rotor angle and depth altered from the FIG. 11a setting to align the beam off-center in the same depth plane as FIG. 11a, and FIG. 11d illustrates an alignment similar to 11c but without a coma-correcting lens, showing the focus aberration problem.

FIG. 13 illustrates in plan and elevation section a transcranial Doppler system capable of rotational beam alignment and translation of the beam baseline to find a window of maximum ultrasound transmission through the skull.

DETAILED DESCRIPTION OF THE PREFERRED EMBODIMENTS OF THE INVENTION

Operating Principles of the Invention

Figure 3A:
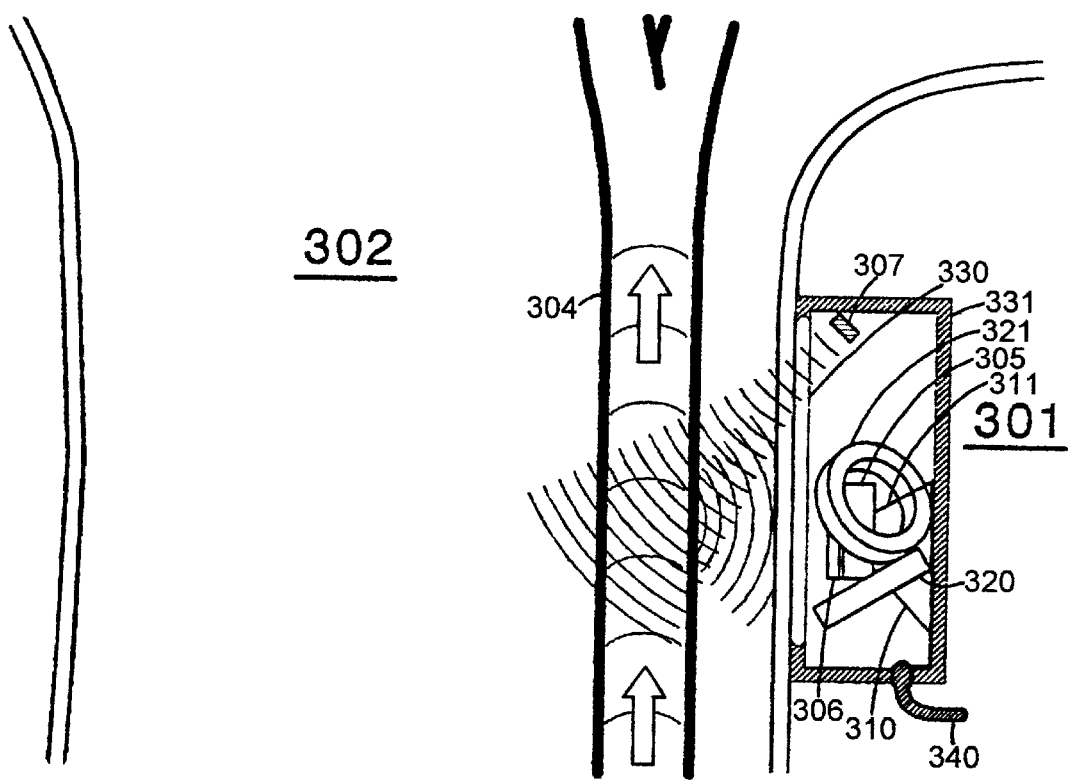

Intermediate in specificity between the "Brief Summary of the Invention" section above and sections below covering specific embodiments, this section concentrates on terminology, basic principles, and the variations in topology that find unified perspective in these basic principles of this instant invention. Key terms that will acquire defined contexts within this application are underlined upon first appearance below.

The ultrasound AimServo is based on a servomotor whose rotor is levitated and moved magnetically in translation and rotation relative to the stator. This servomotor includes multiple variable-field windings and one or more field magnets, which are typically permanent magnets. Actuation forces arise from interactions of winding currents with the field(s) of the magnet(s). The system includes at least one ultrasound transducer, whose beam is aimed by the motions of the rotor and passes through a transmission medium between the rotor and an isolated target volume. To accomplish aiming, either the transducer rides on the rotor, or the beam of the transducer is reflected by the rotor. When a rotor surface functions as a curved mirror, control of rotor position can be used to adjust beam focus.

In designs where the rotor is levitated in an ultrasound-transmitting liquid, it is frequently advantageous to design the rotor for two kinds of buoyancy balance. The first kind is net buoyancy balance in the liquid, such that the rotor is not inclined to float or sink. The second kind is buoyancy moment balance, such that the rotor center of mass is located at the center of buoyancy (i.e. the centroid of the displaced volume) so that there is no gravitational imbalance tending to tip the rotor heavy-side-down. Where the volume for rotor travel must occupy a substantial fraction of the overall volume for the stator/rotor assembly, thus placing restrictions on the electromagnetic design, the electric power demanded to counteract gravity pull on the rotor is often excessive, so buoyancy balance is required. When the premium shifts to design for high angular acceleration of a rotor with little overhead for translation space, coils or magnets packed tightly around the rotor easily overcome gravity, in which case a compact, dense rotor design maximizes angular acceleration capability, outperforming a buoyancy-balanced rotor.

Some or all of the translational and rotational degrees of freedom, or coordinates, of the rotor are controlled by servo feedback, while remaining un-servoed coordinates are maintained within operating limits by passive mechanical and/or magnetic field constraints—if any. In most embodiments, rotor revolution about the axis of the ultrasound beam is inconsequential, so that this rotation coordinate is generally unconstrained and/or ignored.

One of the two components, stator or rotor, includes a primary field magnet, typically a permanent magnet, while the other of the two components, rotor or stator, includes multiple variable-field windings to generate coordinate actuation torques and forces on the rotor, by interaction with the primary field magnet. Thus we refer to moving magnet and moving coil topologies according to whether the design places the primary field magnet or the variable-field windings in the moving rotor. Additional secondary field magnets may be added, opposite the primary field magnet (as the rotor is opposite the stator) to add force or torque bias fields, typically to passively stabilize one or more of the rotor coordinates. For a rotor primary field magnet, one or more secondary field magnet(s) may be located in the stator or, conversely, for a stator primary field magnet, one or more secondary magnet(s) may be located in the rotor. The primary field magnet may be split into two or more separate pieces, though the pieces serve a single field-generation function and are referred to collectively as the primary field magnet.

In the present design context, linear and angular coordinates and the corresponding linear and torsional forces are treated as generalized coordinates and generalized forces, or more briefly as the coordinates and forces of the rotor, regardless of their linear or angular or combined nature. A simplification of computation and conceptualization of generalized forces between a magnet and the field of a winding is the magnetic interaction energy, $E_m$, whose variation with respect to a given coordinate defines a generalized force, be that force linear or torsional or a combination of both. Associated with the primary field magnet is a vector magnetic moment, $M_m$, directed along the north-south axis and of magnitude proportional to the magnet volume multiplied by $B_r$, the residual magnetic field strength characteristic of the magnet material (with a small downward adjustment dependent on the aspect ratio of the magnet and the recoil permeability). By convention in this specification, bold-face is used to designate a vector quantity, such as $M_m$. The same symbol without bold-face represents the scalar magnitude of the vector, e.g., $M_m = |M_m|$. It is generally an excellent approximation to represent the primary field magnet by an equivalent point dipole located at the magnet centroid, i.e., ignoring the details of magnet shape and size and focusing attention on location, strength, and vector direction. Associated with any given variable field winding is a vector field, $B_w$, whose strength and direction at a given point in space is readily determined using a computer summation over finite winding elements: portions of the winding having specified center locations and specified current-length products, in amp-meters, per ampere of coil current. We are concerned specifically with $B_w$ evaluated at the center of the primary field magnet when the rotor is in a specified position and orientation. The terms of the computer summation are based on a common textbook formula that describes vector B-field strength as a function of a vector current element, whose strength has units of amp-meters, and a radius vector from that current element to the point where the field is evaluated. The widely know scalar dot product, or inner product, of two vector quantities, known by the operator"•" or "dot", is used to define a scalar interaction energy, $E_m$:

$E_m = B_w \cdot M_m$ : interaction energy=dot product of winding field with magnetic moment     1]

When the rotor coordinates change in any combination of translation and rotation, the generalized force associated with change in a given coordinate is the slope of $E_m$ plotted as a function of that coordinate. For a specified generalized coordinate location of the rotor (i.e. position and orientation), $E_m$ varies in very nearly linear proportion to the ampere current flowing through variable field winding number "i". We define $X_{bi}$, the beacon coordinate of the rotor with respect to winding "i", as the ratio of change of energy $E_m$ to change of current $I_i$ in variable field winding number "i", using partial derivative notation since $E_m$ also varies as a function of other currents $I_j$ where $j \neq i$.

$X_{bi} = \partial E_m / \partial I_i$ : beacon coordinate=(energy)/(winding current) ratio or slope     2]

A beacon coordinate has units of energy/current, which is joules/ampere in Sl units. A beacon coordinate varies as a function of the physical location and orientation of the rotor in relation to the stator. Consider two coordinate systems: the control coordinates, which are the N coordinate degrees of freedom to be brought under servo control; and the N beacon coordinates corresponding to the currents in N variable-field windings. The partial derivative matrix of beacon coordinates, differentiated with respect to control coordinates, describes the generalized forces, in control coordinates, associated with one-ampere currents in each of the variable-field windings. The product of this generalized force matrix times the vector of N winding currents equals the vector of N components of control force, in the control coordinates, arising from the given winding currents. Every term of this generalized force matrix is, in general, a nonlinear function of the control coordinates. For a given control coordinate location, i.e. for a given position and orientation of the rotor, one can solve for the N variable-field winding currents required to produce a desired vector of N generalized control forces. The solution is obtained by inverting the generalized force matrix and multiplying this inverse matrix by the vector of control forces, yielding the vector of variable-field winding currents. From this description, it is evident that the practicality of such a servo system demands that the generalized force matrix be non-singular, and not too close to singular, for any rotor location within the operating range of control coordinates. A near-singular matrix implies an inverse matrix with large terms, which in turn implies a demand for large control currents to achieve prescribed generalized forces. In practical terms, control forces of adequate magnitude must be achievable without excessively large control currents. In the process of analysis to determine a practical coil configuration for an AimServo system, therefore, the engineer is advised to compute, or at least approximate, the generalized force matrix associated with a proposed coil design and for one or more rotor locations, in order to determine whether the system can be operated within practical limits of coil current and power dissipation.

The utility of beacon coordinates to the instant invention is twofold: that beacon coordinates define a measure of rotor position, and that beacon coordinates define the relationship between variable-field winding currents and control forces. This utility is realized, in practice, only for winding designs for which the generalized force matrix is not too close to singular for any and all rotor positions within the control range. If this criterion is fulfilled, meaning in practice that needed forces can be achieved without excessive winding currents, then the non-singularity of the generalized force matrix implies that there is a continuous mapping from beacon coordinates to control coordinates. From the practical standpoint of designing a servo control system, this means that there is a way to use beacon coordinates to determine the position and orientation of the rotor in space. This result is useful since there is a straightforward way to measure beacon coordinates electronically.

Note that the beacon coordinate definition applies equally to moving magnet and moving coil topologies. When the rotor moves in any combination of translation and rotation, the magnetic coupling of energy between a given winding and the primary field magnet changes, whether it is the winding or the magnet that has moved with the rotor. The generalized force computed for the rotor is correct in either case.

To measure beacon coordinates in a practical AimServo system, a beacon coil is provided concentric with the center of the primary field magnet and aligned to the magnetic moment of that magnet, so that the DC and AC dipole moments are congruent in position and orientation, though not matching in scale since the AC field is inevitably weaker. An AC carrier current is then applied to the beacon coil, which has the effect of adding an AC ripple to the steady component of the magnetic field of the primary field magnet. In an AC position sense topology, this oscillatory magnetic field is called the beacon field. (In a DC position sense topology, the beacon field is the field of the primary field magnet, as discussed later.) For a specific choice of coil current driving the beacon coil to generate the beacon field, one can characterize the strength of the beacon field as the root-mean-square (RMS) amplitude, $M_b$, of the magnetic moment of the beacon coil. (This RMS amplitude would typically characterize a sinusoidal carrier current but could equally characterize non-sinusoidal and even random carrier signals.) In relation to the steady magnetic moment magnitude $M_m$ of the primary field magnet, the ratio $M_b/M_m$ describes the ratio of oscillatory to steady magnetic field strength that will be encountered anywhere in the field of the primary field magnet plus the beacon coil, provided that the magnet and coil are aligned and share the same center. In practice, this ratio may be determined by computation or by direct measurement (e.g., with Hall effect devices). The beacon field induces an oscillatory voltage, $V_{oi}$, in a specified winding "i", dependent on the rotor generalized coordinates. The time integral of this induced voltage has units of volt-seconds, or equivalently, volt-amp-seconds/amp= joules/amp. The time integral of $V_{oi}$ may be represented as $V_{oi}/s$, where for the special case of a sinusoidal beacon field, s is the imaginary angular frequency $s=j\omega$, and for the general case covered by LaPlace transform notation, 1/s is the LaPlace operator for time integration. If the integral of the induced oscillatory voltage in winding "i" is divided by the ratio $M_b/M_m$, the resulting quantity is the beacon coordinate $X_{bi}$. These relationships are summarized by the following mathematical notations:

$$X_{bi}=(V_{oi}/s)/(M_b/M_m) : \text{beacon coordinate varies as induced oscillatory voltage integral referenced to phase of beacon magnetic field} \quad 3]$$

The magnetic moment of the beacon coil, $M_b$, varies in direct proportion to the beacon current, $I_b$, driving that coil. Defining $I_m$ as the steady beacon current that would cause the magnetic moment of the beacon coil to match that of the primary field magnet, we have $M_b/M_m=I_b/I_m$, which leads to another expression for a beacon coordinate:

$$X_{bi}=(V_{oi}/s)/(I_b/I_m) : \text{beacon coordinate varies as induced oscillatory voltage integral referenced to phase of beacon current} \quad 4]$$

The ratio of ratios on the right of Eq. 4 remains the same if we take the time-derivatives of the numerator and denominator of the outer ratio, which in LaPlace notation is equivalent to multiplying through by the differentiation operator "s":

$$X_{bi}=V_{oi}/(sI_b/I_m) : \text{beacon coordinate varies as induced oscillatory voltage referenced to phase of derivative of beacon magnetic field} \quad 5]$$

Note that the voltage amplitude $V_{oi}$ needs to be defined in a manner consistent with the amplitude $M_b$, e.g., an RMS signal in both cases, for the equation to be correct. Note further that $X_{bi}$ was defined as an energy/current ratio in Eq. 2, while Eqs. 4 and 5 define different ways of measuring the mutual inductance between the beacon coil and a chosen variable-field winding. To prove that Eqs. 4 and 5 are equivalent to Eq. 2, we refer to the theory of transformers, which derives from the more general theory of two-terminal networks. In a transformer, the mutual inductance M relates voltage at one terminal to time derivative of current at the other terminal, and the same coefficient applies going from primary to secondary and from secondary to primary: $V_a=M(dI_b/dt)$, where a and b, for primary and secondary, may be interchanged. Relating mutual inductance M to energy E, the cross-product energy in a transformer carrying primary and secondary currents $I_a$ and $I_b$ has been shown to be $E=M(I_a)(I_b)$. A transformer is formed between the beacon coil and the variable-field winding number "i", whose mutual inductance is $M=V_{oi}/(dI_b/dt)$, or $M=V_{oi}/SI_b$, where the second form uses the LaPlace operator "s" to indicate differentiation. This mutual inductance is the energy per ampere of beacon coil current per ampere of variable-field winding current. We have defined $I_m$ as the current that, flowing through the beacon coil, would cause the dipole-moment of the beacon coil to match that of the permanent magnet. Then the product $M \cdot I_m$ is the energy per ampere of variable-field winding current, when the beacon field is equivalent in strength to the permanent magnet field. But this energy-per-ampere figure is our original definition of $X_{bi}$ from Eq. 2, so we write $X_{bi}=M \cdot I_m$. Substituting the next-earlier expression for M in this paragraph yields $X_{bi}=(V_{oi}/sI_b)(I_m)$, or rearranging, $X_{bi}=V_{oi}/(sI_b/I_m)$, which is Eq. 5, and Eq. 5 was previously shown to be equivalent to Eq. 4.

A time-varying mutual inductance is easy to measure and track over time, so the beacon coordinate system provides an easy way to measure the multiple time-varying coordinates of the rotor in this AimServo invention. From a system design standpoint, the beacon coordinates, through their derivatives with respect to the rotor generalized coordinates, provide a complete description of the current/force couplings of the servo system.

Eqs. 4 and 5 define, in mathematical generality, the basis for a class of signal processing operations or methods or algorithms that yield values for beacon coordinates, based on measurements derived from the drive coils during beacon coil excitation. Interpreting Eq. 4 in practical terms, $X_{bi}$ is determined by measuring the AC signal produced in a current-sense resistor, inductor, or transformer in series with the variable-field winding or across a separate winding wound with the variable-field winding; transforming that sense signal in amplitude and phase into a representation of the time-integral of the voltage induced in the winding by the beacon field (taking account of the resistance and inductance of the variable-field winding and output impedance of the amplifier driving the variable-field winding); correlating this time-integral voltage with the time-varying beacon coil current (as a demodulation and smoothing process); and scaling the smoothed result by the factor $1/(I_b/I_m)$ and other such scaling factors as may be useful to scale the final beacon coordinate representation. Instead of correlating a time-integral of an induced voltage with a current, Eq. 5 states that one can correlate an induced voltage with the time-derivative of a current, leading to a procedural description analogous to the previous sentence. In general, one can compute beacon coordinates in terms of any phase-corrected correlation that measures variable mutual inductance. In the case of a steady periodic or sinusoidal beacon field, the correlating process over the time integral voltage may conveniently take the form of synchronous demodulation. The simpler demodulation process of non-synchronous amplitude detection also works, provided that a sign reversal is made in the amplitude signal when there is a phase reversal in the AC signal that is subject to amplitude detection. If the beacon coordinate never changes polarity, then no sign correction is needed for non-synchronous amplitude detection. An advantage of synchronous demodulation or some other continuous-product correlation over non-synchronous amplitude detection is the better noise rejection of the former approach.

In simple winding topologies and for moderate excursions of position and angle, it is found that beacon coordinates often approximate Cartesian coordinates of translation and the direction cosines of angle, i.e., the projections of a unit vector, aligned to the magnetic moment axis, into the plane perpendicular to the nominal center alignment of the magnetic moment axis. In a concrete example of a rotor for transcranial Doppler ultrasound, where clinical constraints call for windings confined to a small volume asymmetric to one side of the volume of rotor motion, the mapping from beacon coordinates to more familiar and convenient rotor coordinates is highly non-linear and non-orthogonal.

The above description has been based on a minimum set of N variable-field windings to drive and measure N degrees of freedom. More generally, the variable-field winding system may include N electronic actuation channels and more than N variable-field windings, with certain windings wired together (e.g., in series or parallel) to share a single electronic channel, in which case physically separate windings wired together may be treated as a single winding for calculating beacon coordinates and actuation forces. Adding complexity, there may be more than N channels of actuation and/or beacon coordinate sensing, employed in a more complicated controller scheme. For example, sensing and control can shift smoothly or in a jump from one winding to another as the rotor moves from the vicinity of one winding to the vicinity of the other. Where more than N channels are used to control N degrees of rotor freedom, the extra control degrees of freedom thus gained may be "spent" satisfying additional constraints, e.g., the minimization of power consumption. Expanded control schemes involving extra channels for control and/or sensing are subject to non-singularity constraints analogous to those described above for an N-by-N control situation.

In certain embodiments of this invention the rotor can be free-floating, while in other embodiments it is necessary to include an umbilical cable to carry signals between the stator and the rotor. The variations in topology of the system fall into two broad categories: ultrasound topologies, and magnetic servo topologies. The two categories are now considered separately, recognizing that in broader engineering contexts, choices made in one category will influence choices made in the other category.

Untethered Beacons

Under most circumstances, moving magnet topologies are preferred for the elimination of multiple electrical connections to the moving rotor. It the rotor is a passive ultrasound mirror, then there is strong incentive to eliminate all mechanical couplings to the rotor and achieve untethered levitation. Two approaches to untethered levitation are DC magnetic position sensing using the primary field magnet as the beacon, and using an induced beacon.

An induced beacon consists of a shorted winding (which may be a multiple-turn winding, a single shorted turn, a conductive ring or disk or any relatively flat continuous conductor in the rotor), functioning as a secondary transformer winding responding to the field of a beacon primary winding in the stator. Translations and rotations of the rotor cause variations in the position and orientation of the AC magnetic field of the induced beacon, which are detected by sensors in the stator. A complication of the induced beacon approach is that the beacon current magnitude is a variable function of rotor position and orientation in the field of the beacon primary winding. A further disadvantage is that external conductors entering the vicinity of the beacon primary winding will perturb the magnetic field of the primary and cause an offset in the decoded coordinates of the rotor. A system using direct wiring to the beacon winding gives a much lower sensitivity to such external perturbations. Despite the disadvantages, the induced beacon approach is highly useful for achieving an untethered rotor.

DC magnetic position sensing, mentioned earlier, eliminates the umbilical beacon wiring in a moving magnet AimServo system, leaving only the ultrasound wiring in a moving transducer system, and leaving no umbilical wiring in a moving ultrasound mirror topology. Using hall effect sensors, which are virtually point sensors in practical circuit packages, one obtains signal couplings whose mathematical description is couched in the comparatively simple equation for the coupling of a point dipole field to a point in space. These couplings to point sensors, however, vary much more steeply and non-linearly than the distributed couplings to coils surrounding a rotor. Thus, in practice, it is difficult sense and map a large range of rotor motions without encountering a singular or ill-conditioned matrix relating perturbations in rotor position/orientation coordinates to perturbations in the coordinates of the multiple sensor output signals. External magnetic fields, including the geomagnetic field, can perturb DC magnetic position sensing. As described later, with an appropriate geometric distribution of sensors including at least three extra sensors above the number of coordinates of rotor motion, it is possible to obtain weighted sums of sensor outputs that measure rotor position and reject interference from external fields. Available hall effect sensors are small, inexpensive, internally amplified, adequately sensitive for practical applications, and simplify other electronic hardware. Hall effect sensors can be scanned directly by a multiplexer into a low-bandwidth analog-digital converter. With no need for hardware of software demodulation of a high frequency carrier, an inexpensive microprocessor suffices to carry out real-time servo control.

Ultrasound Topologies

The AimServo rotor can carry either:

1) an ultrasound transducer or transducer array that translates and rotates with the rotor; or
2) an ultrasound-mirroring region whose changing position and angle alter the beam path.

In the present context, "beam" refers to the path of high ultrasonic energy coupling between an ultrasound transducer and the insonated target volume. Thus, for an outgoing ultrasound pulse, "beam" refers to the path of outgoing energy flux, while for returning ultrasound echoes, "beam" refers to the path of high receptive sensitivity in the ultrasound transducer. For reasons relating to fundamental symmetries of physics, the "beam" defined by a pattern of emitted ultrasound energy corresponds closely to the "beam" defined by sensitive reception of reflected signals. In this patent disclosure, therefore, we will use the term ultrasound beam interchangeably as the distribution of transmitted energy and as the distribution of sensitivity to ultrasound echoes. We shall further describe beam alignment as the vector direction pointing outward from the transducer along the center of the beam path. Beam position will refer generally to the position at which a beam path cuts across a reference plane, typically close to the ultrasound transducer, irrespective of directional alignment. Beam focus will refer generally to the depth or range of depths over which the beam energy or interaction sensitivity is concentrated in substantially a minimum cross-sectional area.

Sharpness of beam focus and focusing depth-of-field are interrelated issues pertinent to applications of the AimServo system. As is commonly known with ordinary light-optics cameras, the depth-of-field for near-optimum focus is inversely related to aperture. In the camera context, light wavelength is seldom an issue, since graininess of the film sets a focus resolution at a wider minimum angle than would be imposed by wavelength and diffraction effects. In ultrasound, diffraction is a major factor limiting resolution. As illustrated in FIG. 1, a large aperture with a short depth-of-field is illustrated by the thick aperture curve at the left of 101 and by the thinner curves representing ultrasound waves propagating to the right, converging toward and diverging away from the central region of optimum focus. For the smaller aperture at 102, an analogous illustration shows a much greater depth of field, but also a much poorer optimum focus represented by a much larger minimum beam diameter. At a given depth chosen for optimum focus in the near-field of an ultrasound transducer, beam width varies as the ratio wavelength/aperture. Since the exponential coefficient for attenuation of ultrasound signal strength with depth varies roughly in inverse proportion to wavelength, there arises a practical minimum wavelength for adequate echo reception at a prescribed imaging depth. This minimum wavelength imposition in turn imposes a minimum in-focus beam diameter that varies inversely as ultrasound aperture. As mentioned in the first paragraph under "Brief Summary of the Invention," it is possible to use the AimServo mechanism to image the same target volume from a multiplicity of positions, and then adapting the methods developed for wide baseline interferometry, to combine image data from that multiplicity of positions to achieve the resolution potentially available from a much larger transducer aperture. As will be shown below, the ultrasound optics of the instant invention can also be adapted to achieve an ultrasound aperture that is a substantial fraction of the package diameter, combined with a mechanically adjustable focus depth. While comparable resolution over a range of depths can be achieved using annular array technology, mechanical adjustment of ultrasound focusing with a levitating AimServo rotor offers potential economic advantages, since only a single channel of electronic ultrasound data need be processed, while the cost of designing for mechanically variable focus depth is potentially low.

Concentrating now on the first transducer topology (FIG. 2), where the transducer 1301 rides on the AimServo rotor 1302, it is apparent that rotational alignment of the rotor (double curved arrows 1303) will directly control beam alignment, while translation of the rotor (double straight arrows 1304) perpendicular to the beam path will control beam position. Later, in describing a First Embodiment of the instant invention, we will describe how beam positioning is used to get ultrasound through a relatively transparent window in the skull and how alignment is used, in coordination with positioning, to cause the beam to intersect a target volume along an artery inside the skull. Beam focus in this context is typically fixed, e.g., using the "self-focusing" property in the near field of a flat ultrasound transducer to give a relatively broad near-field depth of relatively good beam focus in an area significantly smaller than the transducer area.

Figure 15:
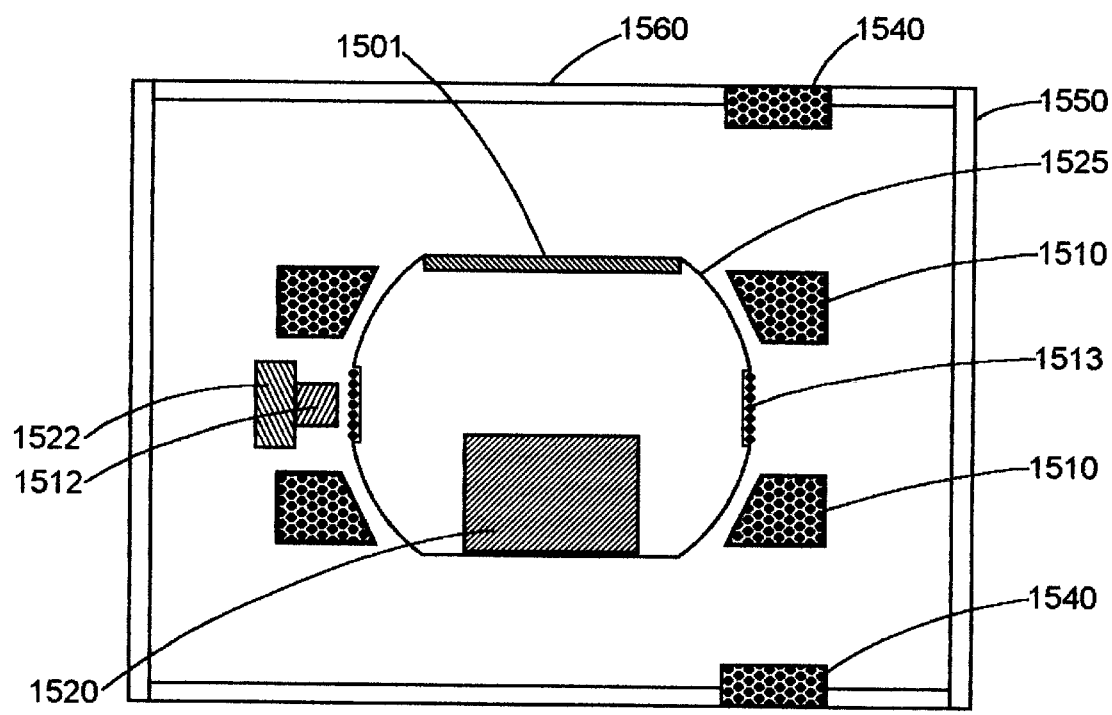
FIG. 15 shows a levitating ultrasound aiming system with transformer coupling of the electrical ultrasound signal between the stator and a free-floating rotor.

In the first topology, electrical ultrasound signals must be coupled between the stator and the rotor-mounted transducer. (Though the transducer is usually employed as both a signal transmitter and receiver, we shall later discuss embodiments in which ultrasound emission and reception take place in separate transducers.) Perhaps the most obvious way to accomplish this electrical coupling is with an umbilical cable 1320 (FIG. 13) between stator and rotor. An alternative approach is transformer coupling between stator and rotor as in FIG. 15: a primary winding 1510 fixed in the stator couples to a secondary winding 1513 in the rotor, which in turn is connected to the ultrasound transducer 1501. In other respects, the system illustrated in FIG. 15 is much like that shown in section in FIG. 9*d*, with a few changes. The corrective ultrasound lens 960 of FIG. 9*d* is replaced by a simple flat ultrasound window, 1560, in front of rotor 1525. The stator-mounted ultrasound transducer 1010 of FIGS. 9 and 10 is, of course, replaced by the much larger flat rotor mounted transducer 1510. To balance the weight of 1510 at one end or the rotor, rotor-centered magnet 910 is replaced by off-center magnet 1520, which is displaced to the end opposite the ultrasound transducer. The rotor assembly can be more or less neutrally buoyant in either case, though the strong electromagnetic coupling of such a compact system reduces the power required to counteract gravity. The coil pair 1510 serving as an ultrasound transformer primary simultaneously serves, at a somewhat lower frequency, as a beacon excitation winding for an induced beacon sensing system. An inductor-capacitor circuit in the rotor series-tunes coil 1510 at the beacon frequency, so that this coil serves double duty as an ultrasound transformer secondary and as an induced beacon winding at the lower beacon frequency. In addition to operation in the ultrasound band and at the beacon frequency, windings 1510 serve as vertical levitation windings. Other coils and secondary field magnets equivalent to those illustrated and labeled in detail in FIGS. 9*a* through 9*d* complete the levitation servo system. For example, rectangular cross-section 1540, seen near the top and again near the bottom of the section view through housing 1550, is part of a large coil loop like that illustrated at 940 in the perspective view of FIG. 9*c*. Permanent magnets 1512 and 1522 correspond to 912 and 922 of FIG. 9*a*, and of course there are other secondary field magnets now shown, to achieve field symmetry at the rotor center.

Concerning ultrasound transformer design tradeoffs, such a transformer will have weak and variable coupling, as the mutual inductance changes with translation and rotation of the rotor. If significant rotor translation is used, the coupling will inevitably be very weak (i.e. the self inductances of primary and secondary will be substantial compared to the desirable mutual inductance) and translation-dependent. If the rotor translations are kept small, as the proportions of the drawing of FIG. 15 suggest, and rotation angles are moderate, then a relatively strong transformer coupling can be achieved. The advantage of transformer coupling is the possibility of eliminating the umbilical chord. Among the disadvantages are poor and variable transformer coupling and increased susceptibility to unwanted high-frequency signal coupling with the environment.

If an umbilical connects the ultrasound transducer to the stator, one can consider a multiconductor umbilical connected to an annular array transducer. This configuration can use a large-area ultrasound transducer while active focusing achieves a narrow focus width. While a transmitted pulse beam is limited in depth-of-field, it is well known in the art that dynamic adjustment of the time delays applied to signals received on the various annuli can result in optimized receiver focus over a range of depths.

Figure 9D:
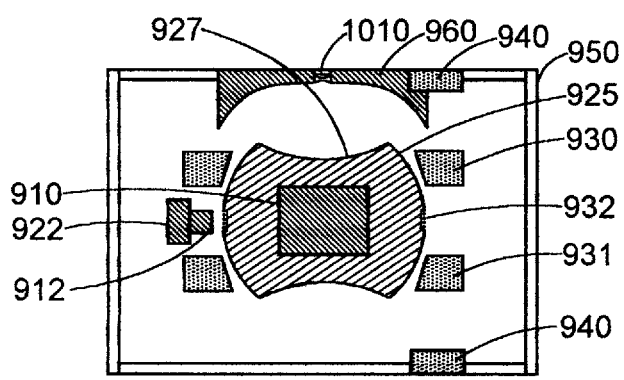
Figure 10:
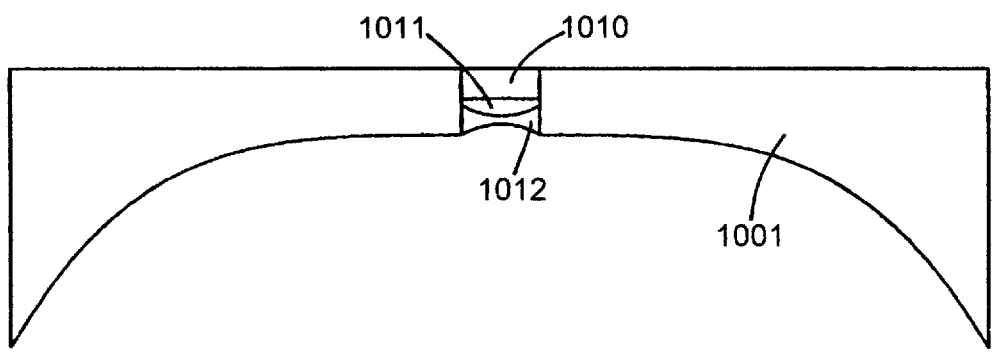
FIG. 10 illustrates details of the ultrasound window and transducer assembly of FIG. 9d.
Figure 11A:
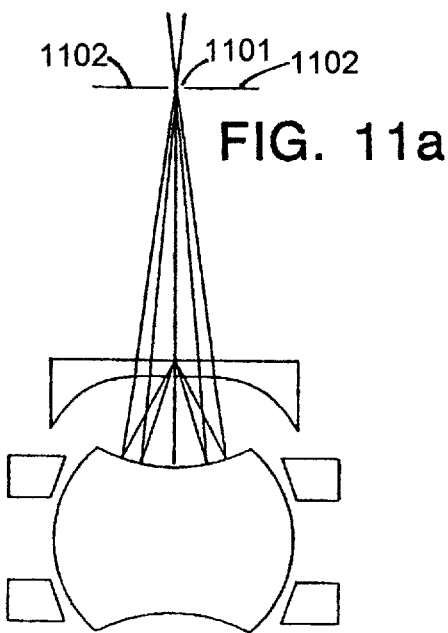
FIGS. 11a–11d are ray tracing diagrams illustrating alignment and focus in the variable-focus embodiment.

Moving on to the second category of ultrasound topologies, FIG. 10 illustrates a fixed ultrasound transducer 1010, viewed in better perspective in FIG. 9*d*, aiming at ultrasound mirror surface atop rotor 925. A concave focusing mirror is illustrated here, though a flat mirror with a focusing transducer is a fixed-focus variation. It is apparent that smaller rotation angles are required for a given beam angle range due to the doubling of angular changes going from the incident to the reflected beam angle as the rotor tilts. The rotor itself is not encumbered with an ultrasound umbilical. A fixed ultrasound transducer of appropriate scale can be an annular array for better focusing over a range of depths. As illustrated in FIG. 9*d*, however, a small ultrasound transducer 1010 gives a divergent beam that bounces off concave focusing mirror 927 of rotor 925, coming into focus in the vicinity of 1101 as illustrated in FIG. 11*a*. This particular rotor is designed for axial translation and two-axis rotation, where the translation alters the depth of optimum focus while the rotation alters beam alignment. Corrective acoustic lens 1001 minimizes focus aberrations for beam angles significantly off the central axis of the assembly, employing principles long known from Wright telescope optics.

Magnetic Servo Topologies

The magnetic servo topologies fall into two broad areas: moving magnet, and moving winding. Moving magnet topologies are generally preferred since they minimize electrical signal connections to the rotor.

A moving coil topology is mentioned here in passing. Understanding the principles described elsewhere in this application for attaining dynamic levitation and translational/rotational control, and given the symmetry of forces between magnets and current-carrying windings, it is clear that the permanent or steady field can reside in the stator, while currents in multiple rotor windings control the multiple degrees of freedom of rotor motion. Two obvious drawbacks to this approach, however, are a flexing multi-conductor tether and magnet expense. The magnetic force per watt obtainable with interacting windings and magnets varies roughly as the product of the two interacting masses over a range where the two masses are of comparable magnitude. Thus, if the magnet material is expensive and the winding material is inexpensive, one can greater weight on the winding side and achieve the same magnetic force per watt at a reduced cost. The rotor of a levitating system typically needs to be smaller than the stator. Therefore, good economic criteria would dictate a smallish magnet in the rotor and much larger windings in the stator. There may nevertheless be circumstances that favor a moving coil rotor.

A five degree-of-freedom moving magnet topology is illustrated in FIG. 13. This design, which will be described in greater detail later, requires a very nearly neutrally buoyant rotor 1302 in order to levitate within reasonable power limits, given the very small amount of space allocated to windings, design proportions chosen for package compactness and a relatively large range of rotor motion. Tether cable 1320, carrying ultrasound signals between stator and ultrasound transducer 1301, needs to be extremely flexible to avoid too large a spring restoration: excessive spring forces cannot be overcome within acceptable drive-coil power limits. In part because of radio frequency environment issues and in part because of the low system cost a hall effect sensing. Hall effect sensors are available with internally preamplified high level outputs that can be applied directly to an analog/digital front end with minimal circuitry overhead. Magnetic fields measured essentially by point sensors are, however, much harder to decipher mathematically for control purposes than AC beacon fields, which provide a direct measure of beacon coordinates.

Description of a Fixed Focus Embodiment

The present invention is shown in a typical application in FIG. 3a, wherein pulsating carotid artery diameter and flow velocity are monitored simultaneously and continuously, so that total volumetric flow rate can be computed over time. Methods and apparatus for tracking arterial diameter over time described in Seale's U.S. Pat. Nos. 4,646,754 and 4,771,792 are reviewed briefly here. For causing transducer alignment to track the direction of maximum return of a desired echo signal, these two earlier patents describe an approach using measured phase differentials between electrically isolated regions of a piezoelectric transducer to indicate alignment error. The current disclosure describes an "alignment dither" approach that works with a simpler transducer and electronics. Then this disclosure shows how to add continuous Doppler velocity tracking simultaneous with diameter tracking, using an unfocused Doppler emitter in addition to the servo-aligned pulsed emitter/receiver transducer. The tracked diameter can be used as a continuous measure of blood pressure after calibration against a standard, e.g., a cuff measurement, or against a vibrational determination of pressure as described in the two earlier cited patents by Seale.

In a carotid-tracking application, ultrasound device 301 is affixed to the neck 302 of a subject by an elastic webbing strap in the vicinity of common carotid artery 304. Device 301 includes a rotor consisting of magnet 305 and ultrasound transducer 306, which serves as a servo-aimable emitter/receiver of ultrasound waves. Device 301 also includes fixed ultrasound transducer 307, which serves as an emitter of a Doppler carrier signal and is defocused so that carrier waves illuminate the entire region where the beam of transducer 306 is likely to have a perpendicular intersection with artery 304 over a range of subjects. One way to achieve a defocused sound pattern is to make the lateral dimensions of transducer 307 comparatively small, down to one ultrasound wavelength for beam dispersion over an entire hemisphere. Transducer 306 is unfocused and is operated in pulsed depth-image mode. When its approximately cylindrical near-field beam is aligned nearly perpendicular to the target artery 304, specular echo responses from the near and far inner walls of the carotid, where the wall surfaces are locally coplanar with the sound wave fronts, approach a maximum strength. The torsionally compliant suspension of the rotor utilizes a tripod of thin flexible wires 310, 311, and 312 (this last not visible). Magnetic torques to tilt the rotor arise from the magnetic fields of coils 320, 321, and 322 (this last not visible) interacting with permanent magnet 305. Transducers 306 and 307 look through acoustically-transparent window 330 in housing 331. Cable 340 and its branchings inside housing 331 carry ultrasound and magnetic drive/sense signals between assembly 301 and a controller/imager unit.

Initially, transducer 306 is caused to scan an angular sector cutting across the carotid, and the operator observes a display of echo amplitude as image brightness in depth-azimuth screen display 360. By moving a joystick fore and aft, the operator tilts the scan sector in a direction perpendicular to the scanning direction, here called the scan elevation angle, causing the scanning plane to pass from one side to the other through the perpendicular across the artery. The operator finds the approximate scan elevation angle at which two oppositely-pulsating echoes 361 and 362, indicative of the near and far surfaces of the carotid artery, are received at maximum amplitude. Moving the joystick from side to side tilts the scan sector azimuth range while maintaining the same elevation angle, so that displayed wedge image 365 appears to rotate about the center of the wedge. Cursor line 370 passes radially through the center-angle of the displayed wedge, so that the operator can center the pulsating wall echo on the cursor line while simultaneously achieving an elevation angle for approximately maximum echo response.

With this two-dimensional angular centering accomplished, the operator instructs the control computer to terminate scan mode, and the ultrasound beam is set for a fixed alignment in the direction that was indicated by the cursor line. The display now changes to resemble an oscilloscope trace flipped 90° from the traditional orientation, so that the trace sweeps down from the top, with left-right deflections from the original cursor line representing negative-positive ultrasound wave responses. For continuity, the depth scale of vertical cursor line 370 remains the same through the display-mode switch. Two oppositely-pulsating wiggles on the trace (not shown, since the display is illustrated in sector scan mode rather than oscilloscope depth-trace mode) represent the near and far wall echoes to be tracked. The operator identifies the depth regions to be tracked via joystick control, moving screen cursors up and down the vertical center-axis of the screen, and phase-lock-loop tracking circuitry locks onto zero crossings in the two echo complexes, yielding an analog voltage that varies as a function of the time interval between the tracked zero-crossings, e.g., using circuitry described in Seale's U.S. Pat. No. 4,771,792. This analog voltage is digitized to give a high-resolution measure of pulsating diameter.

Once depth tracking is underway, the signal amplitudes in the vicinity of the two tracked zero crossings are measured, e.g., by analyzing the digitized echo samples obtained from a flash A-to-D converter and dedicated dual-port random access memory, as with hardware described in Seale's U.S. Pat. No. 4,771,792. A measure of signal strength is chosen such that alignment is defined to be on target when this measure is at its maximum, e.g., peak echo signal amplitude from a selected wall echo, or the product of the peak echo signal amplitudes from the near and far walls. Transducer azimuth and elevation angles are varied rapidly with time in an exploratory dither pattern, e.g., a small angular ellipse about a central alignment angle. Short-term correlations of signal strength with dither angles in elevation and azimuth define elevation and azimuth error signals, which are incorporated in an alignment-correcting servo algorithm driving the central alignment angle so that the error signals are pushed toward zero. The scale factor relating the alignment error signal to alignment perturbation angle depends on the direction of the perturbation angle and on the nature of the target. Angular sensitivity is greater for deflection in the plane that includes the artery axis, less in the cross-axis plane. Angular sensitivity is typically quantified for two reasons: first, to calibrate the alignment-correction algorithm to achieve the gain that gives quickest settling; and second, to determine the direction of the artery axis for Doppler calibration, given that the artery lies in a plane perpendicular to the aligned beam but in an initially unknown direction within that plane.

Suppose that any azimuth-elevation angle alignment is represented as a vector X=(x,y) and that the signal strength measure to be maximized is represented as Z(X), i.e. scalar Z as a function of vector X, which can be visualized as a surface at varying height Z above the (x,y) plane. At any moment, the alignment controller defines a coordinate Xc that represents center-alignment, and the controller causes instantaneous alignment to follow a two-dimensional dither perturbation, Xd, so that the instantaneous alignment vector is Xc+Xd. Supposing that a short-term average value of vector Xd is (0,0), then the short-term correlation of Z with Xd is defined as a short-term average of the product of scalar Z times vector Xd. This correlation is a two-dimensional vector indicative of the slope of the Z surface in the vicinity of center alignment Xc. To achieve a maximum Z, the controller drives Xc in an uphill direction as defined by the recent short-term correlation of Z with Xd.

Having found a maximum Z(X) by gradient climbing, the control algorithm seeks to analyze the two-dimensional surface Z(X) in the immediate vicinity of the maximum Z, i.e. near center alignment, by exploration via small dither perturbations. This Z-surface can usually be approximated by a quadratic equation in the variables x and y, i.e. $Z=ax^2+bxy+cy^2+dx+ey+f$, as determined, e.g., by least-squares function fit techniques applied to alignment dither data describing Z(X). If a horizontal plane slices through this surface at a level slightly below maximum Z, the intersection of the Z surface and the plane will be an ellipse whose minor axis points along the direction of maximum sensitivity of signal strength to transducer alignment. This minor axis direction is the direction of the artery axis, as discussed above. The curvature of this quadratic surface in the major- and minor-axis directions is a determinant of alignment controller sensitivity in these directions. For ongoing alignment tracking, the dither path will typically be adjusted to extend farther in the direction of minimum sensitivity of signal strength to alignment, since less directional information is obtained from a given perturbation in this direction. The alignment control algorithm is typically adjusted with respect to sensitivities along the two axes just described so that a minimum settling time is obtained in both axis directions. The details of designing such a servo algorithm and adjusting its gain coefficients for fast settling will be apparent to engineers with servomechanism experience.

To obtain Doppler blood flow velocity measurement simultaneous with diameter tracking, ultrasound transducer 307 is excited with a sinusoidal signal, emitting ultrasound waves that illuminate the area of intersection of artery 304 with the beam of perpendicularly-aligned transducer 306. Moving blood in the artery scatters ultrasound waves that, when detected by perpendicularly-aligned transducer 306, will exhibit a Doppler frequency shift that is inversely proportional to wavelength and proportional to the component of axial flow velocity resolved parallel to the line from transducer 307 to the intersection of artery 304 with the beam of transducer 306. The cosine factor involved in resolving the desired component of flow velocity is readily determined by an algorithm that uses the artery alignment determination described above and the known geometry of transducers 306 and 307 in assembly 301.

Two possible approaches for minimizing interference between the pulse-image mode operation of transducer 306 and the Doppler-mode operation of emitter 307 with aligned receiver 306 are time-multiplexing and frequency channel separation. In the time-multiplex approach, emitter 307 is switched off long enough to permit a pulse transmit/receive cycle for transducer 306, and enough time is allowed after each pulse cycle completion to allow 307 to be turned on and 306 to receive a period of Doppler echo data. In the frequency channel separation approach, the Doppler carrier frequency is set to a harmonic resonance of transducer 306, a frequency of strong response that is outside the fundamental passband used for pulse imaging. Emitter 307 is designed for the chosen Doppler carrier frequency. Pulse transmission and echo reception by 306 and associated electronics utilize the fundamental resonance of 306. A frequency splitter in the receive electronics for transducer 306 notch-filters the Doppler frequency band from the pulse echo processing path and provides a separate Doppler-band output for Doppler decoding. The frequency channel approach will involve some degree of time-multiplexing, since uninterrupted Doppler signal reception is unlikely to be practical during the brief period of pulse transmission by 306. The periodic interruptions in Doppler reception by either approach will give rise to splitting of the Doppler spectrum into multiple frequency bands whose spacing is the pulse repetition frequency. It will be seen that to select a single Doppler frequency band for decoding and avoid overlap with adjacent Doppler images, the pulse repetition frequency must exceed the Doppler bandwidth. If the pulse repetition frequency is made too high, however, there could arise depth aliasing problems in the pulse image mode, as well as failure of pulse echoes to die out before the Doppler reception period in a time-multiplex mode.

Detailed methods for dealing with the frequency separation problems mentioned here are familiar to designers of pulsed Doppler imaging systems, who will recognize that the tradeoffs necessary to obtain good Doppler signal power are much more favorable by the two-transducer approach described here than with the low Doppler duty cycles demanded by single-transducer pulsed Doppler approaches. Pulsed Doppler system designers will also recognize the applicability of other encoding schemes, particularly those involving random noise encoding and decoding by correlation techniques.

Once an alias-free Doppler band is obtained, decoding of the Doppler signal is accomplished using well-known techniques, ideally employing quadrature decoding to distinguish forward and reverse velocities. Doppler spectral analysis can be accomplished using fast fourier transform techniques, with fast digital signal processor (DSP) chips, e.g., the Motorola DSP56001, permitting real-time spectral analysis. Very low Doppler frequencies are filtered out and otherwise ignored because of interference from artery wall motions. Average Doppler frequency over the artery lumen is defined by using Doppler spectral power density as a weighting function to define a weighted frequency average. Average flow velocity is weighted-average Doppler frequency multiplied by half the wavelength of the carrier and divided by the cosine of the angle between the artery axis and a vector from the tracked artery region to the Doppler emitter. This cosine factor is determined from tracking and dither data as discussed above. Volume flow rate is obtained by multiplying average flow velocity by lumen area, based on the ultrasound-tracked diameter. Correction algorithms may be needed if sensitivity of the Doppler receiver is not sufficiently uniform over the artery lumen, which could skew the Doppler spectral distribution.

Note that the functions of Doppler emitter and Doppler detector can be interchanged in the design just discussed, with aimable transducer 306 outputting a Doppler carrier and fixed-alignment transducer 307 functioning as a Doppler receiver. If the carrier signal is to be emitted during periods of pulse-echo reception by 306, then very good frequency channel separation must be provided, so that the high-gain pulse-reception circuitry is not overloaded by the outgoing Doppler carrier.

Figure 3B:
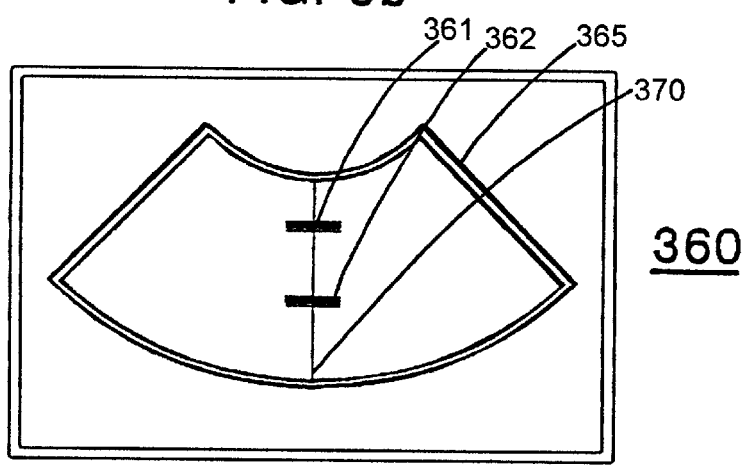
FIG. 3b illustrates an ultrasound display image indicating artery diameter.

It is seen that the system of FIGS. 3a and 3b is useful for monitoring pulse, flow velocity, artery diameter, volumetric blood flow. It will be seen that the operations of identifying and centering a target artery such as the carotid, while described in relation to a hypothetical operator with a joystick, could be performed entirely under digital control with an expert system algorithm, since manual adjustments of the transducer are not needed after appropriate initial placement. The important electromechanical servo device that permits total automation by aligning transducer element 306 quickly and accurately is described later in this disclosure.

Description of a Variable Focus Embodiment

Figure 4:
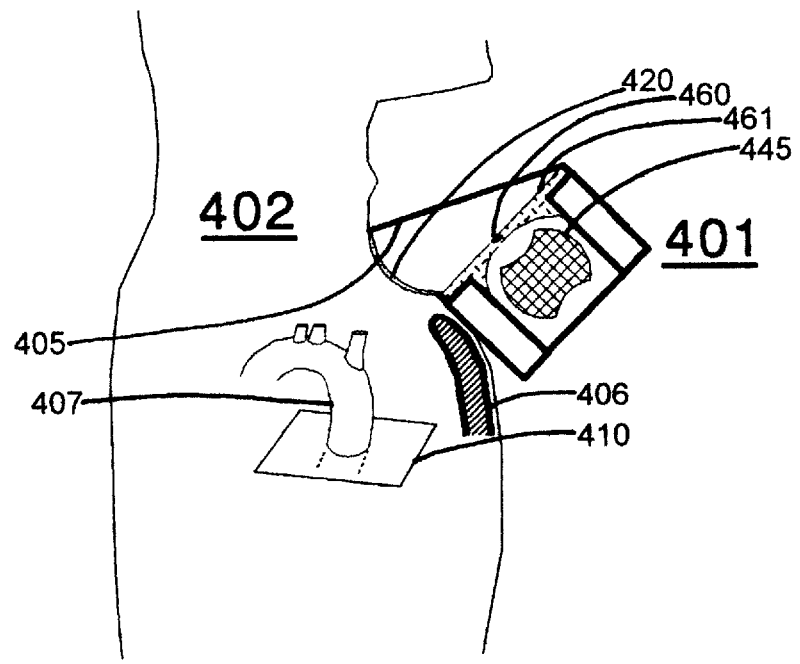
FIG. 4 illustrates a variable-focus beam alignment servo for monitoring cardiac valve timing and blood flow in the aorta.

The present invention is shown in a second application context in FIG. 4. Ultrasound device 401 with two-axis beam alignment capability is affixed in the suprasternal notch on the neck of subject 402 by a harness (not shown), whose elastic bands extend from 401 outward laterally and back dorsally to shoulder loops, rejoining and continuing back dorsally and inward medially to join behind the subject's back. Device 401, viewed schematically in side section, is shown sitting in the concavity of the throat atop the suprasternal notch. A pulsed ultrasound beam, whose alignment is controlled in two dimensions, arises from ultrasound transducer 460, appearing in the scale of this diagram as a dot in the center of ultrasound focus compensating lens 461. The spreading beam from 460 is reflected off a concave face of rotor 445, is directed through lens 461 to ultrasound mirror 405, and from the mirror down, through convex housing window 420, out of the housing, and behind sternum 406 to ascending aorta 407. By means of range-gated ultrasound Doppler, flow velocity is measured in the ascending aorta at points lying roughly within depth-plane 410 and analyzed to obtain a measure of systemic cardiac output. The Doppler beam is focused automatically at the range-gated depth. The principles of device 401 will be explained later with reference to FIGS. 9a through 9d, describing a device similar to 401 except lacking ultrasound mirror 405 and having the counterpart of ultrasound lens 461 (lens 960 in FIG. 9d) serving also as the window from the housing into the body. Note that the spaces in the housing surrounding rotor 445 and enclosed by mirror 405, window 420, and lens 461, are filled with an ultrasound transmission fluid.

While it is well known to monitor velocity in the ascending aorta in comparable fashion using a hand-aligned ultrasound device, the present invention offers substantially more capability than before. Combining range-gating ability with a new capability for rapid software-driven two-axis alignment control and two-dimensional autofocusing, the device can accurately map the solid angle representing the aortic cross-section at the gated depth, and by varying the gating depth and re-mapping the cross-section, the device can map the angle of the ascending aorta with respect to the ultrasound device over the vicinity of flow monitoring. For a substantially continuous monitoring of flow velocity distribution with diameter determination and automatic centering of the scan pattern, the transducer beam can be made to trace, e.g., a figure-8 pattern on plane 410, extending slightly beyond the limits of the lumen of aorta 407 at the range-gated depth. The points on the figure-8 where Doppler reception drops to zero define both artery diameter and scan centering, while the distribution of velocities with respect to radius from artery center and with respect to time can be used to estimate total volumetric flow. The scanning loop is traversed at a high enough frequency, e.g., 15 Hz, that the two passes per loop across the artery give adequate updating of flow velocity and diameter to resolve time-domain waveforms of pulsating diameter, velocity, and volumetric flow. By varying the range-gating depth, effectively raising and lowering the imaging plane 410, and re-mapping the velocity profile to redefine the aortic cross-section, the 3-dimensional shape of the ascending aorta can be mapped and the angle between its flow axis and the ultrasound beam axis defined with precision at a given range-gate level, so that an appropriate cosine correction factor can be applied to the Doppler data to obtain absolute velocity components. For integrating over the observed cross-section to obtain flow, however, the cosine correction is not used, since what is wanted is the component of blood flow velocity resolved perpendicular to cross-section plane 410, over which the area integration is performed to obtained flow. If plane 410 is perpendicular to the ultrasound beam axis at the artery center, then the Doppler-measured velocity is the desired velocity component for integration.

This capability is similar to that of the linear array scanning system described by Aronson in U.S. Pat. No. 4,103,679 (noted in BACKGROUND section), except that with two-axis control, the system described here can locate and track its target in a three-dimensional volume over time without operator intervention, whereas Aronson's one-dimensional scanning system is an accurate estimator of diameter and flow only when the operator succeeds in causing the scan plane to slice accurately through the artery lumen along the central axis. The operator must achieve this alignment relying on visual feedback from a pulsating cross-section image.

A commonly-used continuous aortic flow monitoring system of past art uses three separate ultrasound devices: a Doppler velocity device hand-held at the suprasternal notch to detect velocity somewhere in the ascending aorta; a B-mode pulse imaging device obtaining a cross-section of the ascending aorta from between two ribs, the area of which is determined by operator placement of cursors on the screen image; and a continuous Doppler device located in the esophagus and monitoring flow in the descending aorta. A one-time computation of cardiac output is based on flow and cross-section data from the first two sensors during a few heartbeats. This output is assumed to remain proportional to short-term-average flow velocity from the third, esophageal sensor, whose output is used for continuous monitoring. Besides the cumbersomeness of this approach, the accuracy is questionable, since a substantial fraction of total cardiac output goes to the upper body and head while the remainder, probably a significantly varying fraction of the total, is monitored in the descending aorta.

As with the carotid diameter and flow monitoring system of the first embodiment, this aortic monitoring system can be used for continuous pressure waveform monitoring when independently-measured blood pressure is calibrated as a function of measured aortic diameter. While the definitive calibration is with an aortic catheter, a cuff calibration system yields useful results with the considerable advantage of non-invasiveness.

The fixed and variable focus embodiments of the invention, described with emphasis on the ultrasound application above, are reexamined below with emphasis on the beam alignment electromechanics and control methods.

Beam Generation and Alignment in the Fixed Focus Embodiment

Figure 5A:
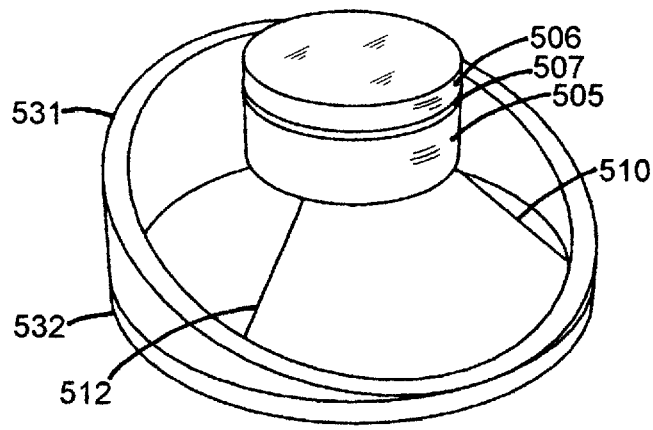
Figure 5B:
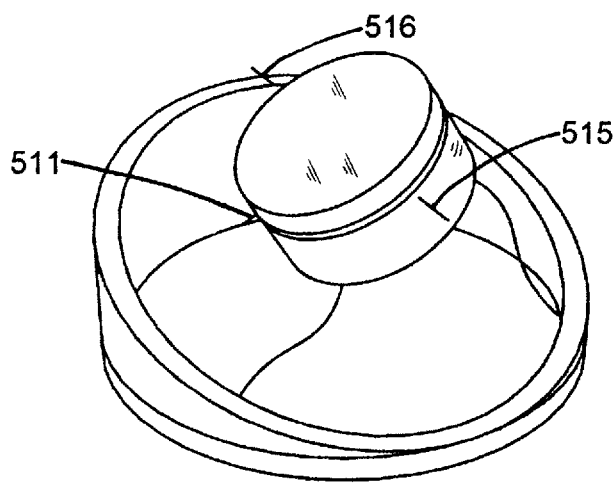
FIG. 5b illustrates the same components in rotated alignment.
Figure 5C:
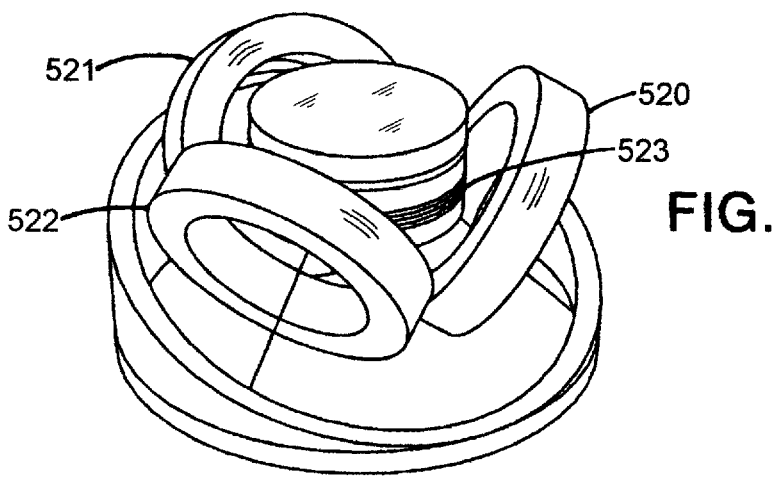
FIG. 5c illustrates the addition of magnetic drive s and a position-sense to the assembly of 5a and 5b.

The electromagnetic and acoustic components from assembly 301 of FIG. 3a that achieve variable beam alignment in this first embodiment are shown in greater detail in FIGS. 5a, 5b, and 5c, here shown mounted in a cylindrical housing rather than in the larger rectangular housing 331 of FIG. 3a that includes a Doppler emitter transducer. This cylindrical housing, illustrated mostly cut away, consists of cylindrical wall 531 (shown cut open), flat base 532, and an ultrasound window 530 above, removed entirely for this illustration. The ultrasound beam in this embodiment is typically neither focused nor defocused, but approximates a columnar beam in the near field, as it arises from the flat transducer surface. The rotor assembly is supported on a flexible wire tripod, which lends comparatively high rigidity against translation and high compliance to rotation. As shown in FIG. 5a, the rotor consists of puck-shaped permanent magnet 505, thinner ultrasound transducer disk 506 of the same diameter as the magnet and axially centered above the magnet, and thin acoustic decoupling layer 507 between magnet 505 and disk 506. Magnet 505 and disk 506 correspond to 305 and 306 of FIG. 3a.

Ultrasound transducer disk 506, whose separate layers are not shown in the figures, includes an active piezoelectric disk for transducing between electrical and mechanical energy, plus passive acoustic layers laminated to the disk to modify its damping and acoustic coupling properties. For a rapid settling pulse response, the piezoelectric disk may be backed with an acoustic absorbing layer, though this layer is omitted in this preferred embodiment, as it is often omitted in designs where high sensitivity and transduction efficiency are more critical than fast settling. The front side of the disk consists typically of one, two, or three impedance-matching interface layers, depending on bandwidth requirements— three layers in this embodiment. These layers are each about one-quarter wavelength thick at the center frequency of the transducer, and the layers provide progressive steps from the high acoustic impedance of the transducer to the low acoustic impedance of the ultrasound transmission fluid inside the housing. With high-efficiency piezoceramic transducer disks, the acoustic impedance ratio from ceramic disk to fluid is typically about 15 to 1, so that without interface layers, acoustic energy couples poorly and the transducer tends to ring. The piezoelectric polymer Polyvinylidene Difluoride, or PVDF, has a much lower acoustic impedance, so that interface layers are not essential, but the electroacoustic transduction efficiency of PVDF, especially in thickness mode, is quite low, presenting potential signal/noise problems. Also, PVDF has a high electrical impedance, necessitating especially high drive voltages to inject sufficient signal energy. For these reasons, a piezoceramic transducer is chosen in preference to PVDF for this preferred embodiment, with three acoustic interface layers and no backing layer.

Minimum pulse width varies typically as the reciprocal of absolute bandwidth (i.e. in Hz, not a frequency ratio), so transducers of high center-frequency and high relative bandwidth (i.e. ratio of maximum/minimum $-3$ db frequencies) yield the highest depth resolutions. Excessively high design frequencies lead to excessive ultrasound attenuation in tissues, so that signal/noise performance is traded off against the high resolution possible at high frequencies. Since ultrasound scattering from blood tends to be weak at low frequencies and to increase as the fourth power of frequency, signal/noise performance for Doppler flow detection tends to improve with increasing frequency up to a point where transmission attenuation begins to dominate rapidly. Aside from the issue of depth resolution, imaging of specular reflections off artery surfaces for diameter tracking tends to be easiest and give the best signal/noise performance at lower frequencies than are optimum for Doppler flow detection. Therefore, in this embodiment, the pulsed echo system for tracking artery diameter and maintaining perpendicular alignment operates around a 4 MHz center frequency with broad bandwidth, while the Doppler carrier frequency is placed in the vicinity of the transducer's third harmonic resonance, around 12 MHz, which is the center frequency for Doppler emitter 307 (FIG. 3a).

Decoupling layer 507 is of low density and low acoustic impedance, so that coupling of vibrations from the back surface of the piezoceramic disk is very low. The layer consists of balsa wood for this preferred embodiment, though a plastic foam such as polystyrene would fulfill the same function. A plastic film wrapped around the cylindrical surface of the rotor assembly prevents ultrasound transmission fluid from impregnating the porous decoupling disk.

The rotor suspension consists of a tripod of very fine music wire (.1524 millimeter diameter for this preferred embodiment). One tripod leg carries ultrasound signals to and from the transducer disk, one leg carries a high-frequency oscillation for magnetic alignment sensing (see below), and the remaining tripod leg serves as common ground for both ultrasound and alignment sense signals. The legs are numbered 510, 511, and 512 in counterclockwise order as viewed from above. Tripod legs 510 and 512 are visible in FIGS. 5a, b, and c and labeled in 5a, while tripod leg 511 is obscured except in 5b, where a small visible segment is labeled. Attachment of the legs is achieved by crimping short pieces of thick-walled brass tubing to the ends of the wire segments, including connecting pieces of copper wire inside the crimped brass pieces for electrical connections. The crimped-on brass pieces are then cemented into shallow holes in base 532 (detail not shown) and in the bottom of magnet 505. Magnetic torque exerted on permanent magnet 505 causes the rotor assembly to revolve, as illustrated in 5b. With the permanent magnet axially poled, a transverse applied magnetic field tends to align the permanent magnet to the applied field, causing rotation. For small angles, the axis of rotation passes through the point where the lines extending from the tripod legs converge, roughly at the center of the bottom surface of transducer 506. Line segments 515 and 516 illustrate the axis of initial rotation when the magnetic torque vector is aligned in the same direction as the axis drawn. At large rotation angles, changes in end-to-end lengths of the bent wires cause the small-rotation center point of the rotor to drop slightly lower and also to move slightly in a lateral direction, due to differing bending of the three wires associated with a given torque direction. Hence, rotation is only approximately about a fixed point.

The torque-generating magnetic field arises from field coils 520, 521, and 522, respectively surrounding tripod legs 510, 511 and 512, as illustrated in FIG. 5c. The three coils just touch in the symmetry of three equal faces of an inverted isosceles tetrahedron. As illustrated in perspective, the coils are tilted back 30° from a vertical plane. The relative currents applied to the three coils are determined by a 2-to-3 matrixing circuit, operating from two voltage inputs controlling orthogonal axes X0 and X90, in such a way that the applied magnetic field at the center of the permanent magnet is horizontal and points in the desired direction of rotor tilt. The field generated by the three coils could be generated as easily using four coils wired as two connected pairs. The three coil arrangement requires three drive circuits instead of two (only one circuit per coil-pair in a four coil arrangement), but there is an efficiency advantage to three coils. The 30° tilt-back of the coils provides clearance for a wide-angle swing of the ultrasound beam—at least 30° off-axis in any direction for the illustrated assembly. The rotor magnet is centered as low as possible in the three-ring coil cradle, with the magnet center lying below the intersection of the center lines of the coils and comparatively close to the coil centers. In this low position, the inclination from horizontal of a single-coil magnetic field is closer to horizontal than the 30° coil tilt angle, giving a cosine resolving factor quite close to unity. When four coils are used in straight-up orientations, brought as close together as possible so that their edges touch, the rotor magnet is farther from the coil centers in relation to the coil diameters than in the three-coil arrangement, and since the coil field strength drops off rapidly with distance, the magnetic coupling is considerably weaker. If the coils in a four-coil symmetry are tilted back, this further worsens the magnetic coupling situation. It turns out that for a given rotor size and optimum coil proportions, a three-coil arrangement operated at a given wattage generates a significantly stronger field than does a four-coil arrangement, so the three-coil symmetry is chosen in the embodiments detailed here.

A fourth coil, 523, shown in FIG. 5c as a striped band, girdles the moving magnet and is used for sensing 2-D rotational alignment. The high-frequency oscillation signal for magnetic alignment sensing, carried by a tripod lead as noted above, is applied to coil 523, with the other end of the coil winding connected to the ground tripod lead. The oscillating current set up in coil 523, set at about 30 KHz in this preferred embodiment, generates an oscillating magnetic field aligned to the axis of the moving magnet and ultrasound transducer. The components of this magnetic field linking the three drive coils indicate rotational alignment, as described in FIG. 6.

Figure 6:
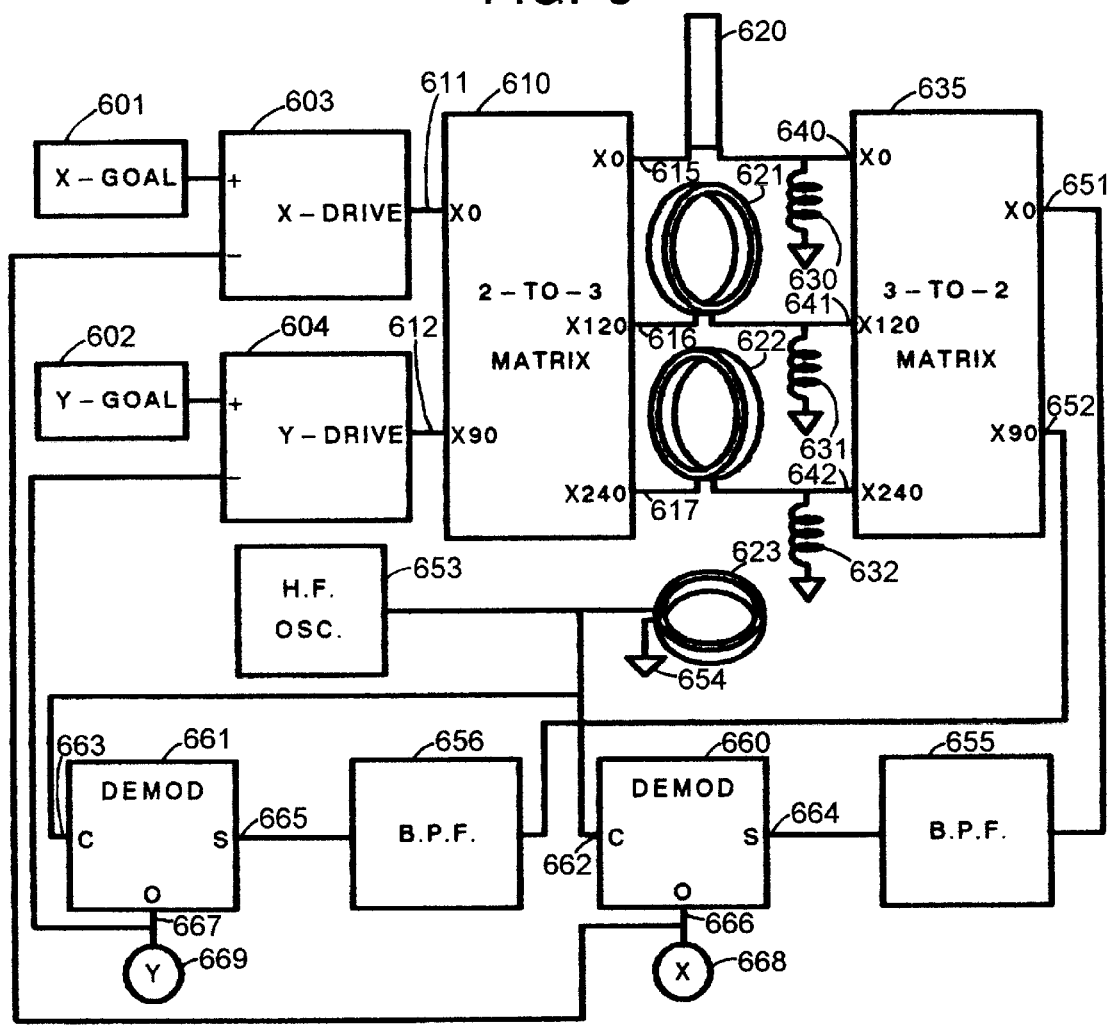
FIG. 6 illustrates electronic circuitry associated with FIG. 5c for angular position sensing and servo control of 2-axis angular alignment of the rotor.

Examining FIG. 6, two primary input signals, X-GOAL and Y-GOAL, at 601 and 602, enter the non-inverting inputs of error signal circuit modules 603 and 604, each of which generates an error signal between a goal input and a sensed response input, transforms that error signal by an appropriate gain transfer function, and delivers a drive output, labeled X-DRIVE and Y-DRIVE for the respective modules. These drive signals enter 2-to-3 MATRIX circuit 610, where they are resolved from two orthogonal input axes, X0 and X90 at inputs 611 and 612, to three 120° symmetry axes, X0, X120, and X240, at outputs 615, 616, and 617. These outputs power the drive coils, 620, 621, and 622 for respective outputs 615, 616, and 617 and corresponding to coils 520, 521, and 522 of FIG. 5c. From the drive amplifiers in the matrix circuit, each coil is series-connected with an inductor coil, 630, 631, and 632 respectively for the three coils, each coil being grounded on the far side. The voltage developed at the junction between each drive coil and its associated series inductor coil indicates the coil current, including a component arising from the drive signal to the individual coil, an additional component arising from the drive signals in the other drive coils as coupled by mutual inductance, and another additional component arising from the high-frequency current in movable coil 623, which corresponds to coil 523 of FIG. 5c. The three coil-to-coil junctions are wired to the inputs of 3-to-2 MATRIX circuit 635 at inputs 640, 641, and 642, designated by the phases X0, X120, and X240, corresponding to the axis labels described for the 2-to-3 MATRIX circuit output but not representing the same signals as those outputs. The outputs 651 and 652, with phase designations X0 and X90 corresponding to the phases of the inputs to the 2-to-3 MATRIX circuit but not representing the same signals, carry AC information about angular position of the rotor. This information arises from the action of high-frequency oscillator 653, marked "H. F. OSC.", driving movable coil 623, this coil having its other end grounded at 654. The signal and ground connections correspond physically to tripod wires discussed in relation to FIGS. 5a, 5b, and 5c. Referring back to FIG. 5c, when the rotor and coil 523 align in a nominal rest position in the plane of symmetry of coils 520, 521, and 522, then the oscillatory signals at 651 and 652 of FIG. 6 are zero, to within design tolerance. A tilt of coil 523 or 623 (for the physical coil of FIG. 5c or the circuit schematic version of FIG. 6) that gives the coil axis a non-zero projection in the X0 direction gives rise to a high-frequency signal at 651 (FIG. 6), designated X0, and similarly a tilt causing a non-zero X90 projection gives a signal at 652. These AC signals are transformed into signed direction cosine signals as follows. The signals at 651 and 652 are each bandpass-filtered at 655 and 656, each labeled B.P.F., with the filters providing maximum gain in the vicinity of the oscillator carrier frequency in addition to corrective phase shift at that frequency to bring the filtered outputs substantially into phase with the oscillator output from 653. This oscillator output serves as a phase reference signal to the carrier inputs of demodulators 660 and 661, each designated "DEMOD" with carrier inputs marked "C" at 662 and 663, signal inputs marked "S" at 664 and 665, and outputs marked "O" at 666 and 667. The signal inputs at 664 and 665 are provided by the bandpass filter outputs from 655 and 656, respectively. Internally, each demodulator effectively multiplies its signal input S by +1 or −1, corresponding to the positive or negative instantaneous polarity of the carrier C and almost irrespective of instantaneous carrier magnitude except at very small magnitudes, and this product signal is lowpass-filtered to give output O, representing the low-frequency-average magnitude and polarity of the frequency component of its S input in phase with the C input. In this circuit, both demodulator carrier inputs "C" are the same output signal from high-frequency oscillator 653 that drives coil 623. The demodulator outputs from 666 and 667, varying in proportion to the direction cosines of tilt in the X0 and X90 axis directions, are designated "X" and "Y" at terminal circles 668 and 669 and are connected to the inverting inputs of respective error signal circuit modules 603 and 604. The feedback action of the servo loop causes angular position sense signals "X" and "Y" to track "X-GOAL" and "Y-GOAL", with the error signal between corresponding sense and goal values generating "X-DRIVE" and "Y-DRIVE", in fulfillment of the function of angle-correcting feedback in a servo loop. The quantities tracked by the loop are the direction cosines of rotor tilt in two directions.

Examining the design for either of error signal circuit modules 603 or 604 as shown in FIG. 7, a goal input, here designated "Z-GOAL" at 701 and representing any goal voltage signal, such as "X-GOAL" or "Y-GOAL" of FIG. 6, is compared with a measured signal input, here designated "Z" at 702 and corresponding to the signal designated either "X" or "Y" for the application described for FIG. 6. The "Z-GOAL" and "Z" inputs 701 and 702 go respectively to the inverting "−1" and non-inverting "+1" inputs of unity gain difference amplifier 710. The output of this amplifier is applied via an input resistor-capacitor network to inverting operational amplifier 720, which has series resistor and capacitor 721 and 722 in its feedback path. On the input side of 720, resistor 723 sets DC-coupled input current from 710 to the inverting summing junction of 720. The series combination of capacitor 724 and resistor 725 is connected in parallel with resistor 723 from the output of 710 to the inverting summing junction of 720. Capacitor 724 in conjunction with resistor 723 determines a phase-lead time constant for input signal currents. The addition of resistor 725 in series with capacitor 724 provides a high-frequency limit for the phase lead of capacitor 724, bringing the circuit phase response back toward zero at high frequencies with a net effective input resistance of 723 in parallel with 725. Feedback resistor 721 to the inverting summing junction of 720 sets the middle-to-high frequency voltage gain for the current to the summing junction, while series feedback capacitor 722 causes integration of the current input to dominate voltage output response at low frequencies. The non-inverting input of amplifier 720 is referenced to ground potential, as indicated at 730. The output of amplifier 720 is designated "Z÷DRIVE" at 750 and serves as the input to the device to be controlled. This output becomes "X-DRIVE" or "Y-DRIVE" for respective outputs 611 and 612 of FIG. 6.

The transfer function from the differential input to Z-DRIVE output 750 is of the form commonly used in servo control feedback loops, with the amplitude response being minimum in a middle frequency range, rising with phase lag at low frequencies due to the integration of feedback capacitor 722 in conjunction with input resistor 723, and rising with phase lead at moderately high frequencies due to the action of input capacitor 724 in conjunction with feedback resistor 721. The moderately-high-frequency phase lead overcomes some phase lag of the driven system, lending high-frequency stability. The band limitation of the phase lead avoids excessive noise gain and overload at frequencies where servo loop gain falls well below unity. The signal integration elbow at low frequencies causes the servo loop to null any DC errors that might otherwise persist. The overall gain of the controller at midband must not be too high or loop instability will result despite the phase lead compensation.

When coil drive and response signals for two tilt axes are generated by three coils, a 2-to-3 matrixing circuit translates x and y signal-vector components into the voltage signals applied to the three coils, and an inverse 3-to-2 matrixing translates the coil responses, whether representing low-frequency drive current response or high-frequency carrier-detecting response, into the x and y signal axes. This matrixing back and forth between symmetries is illustrated in FIG. 8, as accomplished with three summing amplifiers, 810, 811, and 812, for the 2-to-3 matrixing, and two summing amplifiers, 830 and 831, for the 3-to-2 matrixing. Each summing amplifier is typically implemented using a differential input operational amplifier with appropriate resistors from the non-inverting and inverting inputs to input voltages, ground, and the output. Where high input impedance is needed, unity-gain input followers can be added, though these are not necessary in the current context, where the drives are of low impedance from operational amplifier outputs or from fairly low-impedance sense coils. Those familiar with circuit design will readily compute the details of resistor topology and values, topics that do not merit discussion here. The amplifiers are represented here as having specified positive or negative summing gains indicated by numbers on their input sides, using the common triangle symbol for amplifiers.

On the left of FIG. 8, the 2-to-3 matrixing side, inputs 801 and 802 are labeled respectively X0 and X90, indicating a pair of voltages associated with geometric coordinate axes X at angles 0° and 90°. This voltage pair is transformed into a trio of voltages, labeled X0, X120, and X240, at 815, 816, and 817, emerging respectively from the outputs of summing amplifiers 810, 811, and 812. The voltages at 801 and 815 measure about the same but are not identical, even though they are both labeled X0, for voltage 801 is amplified by +1 at amplifier 810 to give voltage 815—a unity-gain amplification that in the current system provides the output current level necessary to drive a magnetic coil. Voltages 816 and 817, called X120 and X240, are weighted sums of X0 and X90 at 801 and 802. The weighting factors for X120 at 816 are −0.5 and +0.866, respectively, for the voltages at 801 and 802, while the weighting factors for X240 at 817 are −0.5 and −0.866 for the same two respective input voltages. The 0.866 figures (+or −) are approximations of cosine(30°), which is actually the mathematical value to target as accurately as needed for the precision of the engineering result.

On the right of FIG. 8, the 3-to-2 matrixing side, the inputs 820, 821, and 822 are labeled the same as 815, 816, and 817, namely, X0, X120, and X240, but these are not the same voltages at all. A label like this indicates the geometric axis with which each voltage is associated. As illustrated in FIG. 6 and discussed, the voltages 815, 816, and 817 are coil-driving voltages, while the identically-labeled voltages 820, 821, and 822 represent voltage differentials across inductive coils sensing the currents of the three drive coils. Voltages 820, 821, and 822 are weighted +0.667, −0.333, and −0.333 by amplifier 830 to give output 835, labeled X0 to indicate association with the same X0 geometric axis as voltages 801, 815, and 820. Voltages 821 and 822 are weighted +0.577 and −0.577 at amplifier 831 to give output 836, labeled X90 to identify it with the same geometric axis as voltage 802. The numerical values 0.667 and 0.333 (+or −) indicate the mathematical fractions $\frac{2}{3}$ and $\frac{1}{3}$, while the 0.577 (+or −) value indicates $\frac{2}{3}$ of cosine(30°).

If the voltage terminals 815, 816, and 817 are connected, respectively, to voltage inputs 820, 821, and 822, then the voltages 835 and 836 will be identical to voltages 801 and 802 to within the accuracy of the amplifiers. If the length of the vector (X0,X90) associated with voltages 801 and 802 is one unit, then the voltages X0, X120, and X240 at 815, 816, and 817 will have peak values of +or − one unit, and the vector sum of the three values on 1200 axes will have a constant length of 1.5 units. The five weighting factors in the 3-to-2 matrix will be recognized as being multiples of ⅔ of the five weighting factors in the 2-to-3 matrix, this scaling-down being used to restore the vector magnitude of (X0, X90) at 835 and 836 to one unit.

The circuitry described in relation to FIGS. 6, 7, and 8 will cause the ultrasound beam to be aligned rapidly to a goal alignment designated by an input pair of direction cosines for the X0 and X90 tilt directions. In a preferred non-focusing embodiment, as employed for example in tracking diameter and flow in an artery as shown in FIG. 3a, the goal alignment arises from a digital computer controller via a Digital-to-Analog or D/A interface. To avoid slewing and severe overshoot of the servo system described, changes in the X-GOAL and Y-GOAL signals should be limited to accelerations consistent with the non-slewing limits of the servo system. It is judged preferable, in the current context, to use a fast and capable control computer equipped with software to generate trackable paths from one target alignment to the next, rather than developing relatively complex nonlinear analog control hardware to anticipate when to "apply the brakes" to avoid overshooting a target alignment. The X-GOAL and Y-GOAL signals include vector components described above as Xc and Xd, center alignment and dither perturbation about that center, for target tracking control in relation to strength of a desired signal. In a scanning mode, X-GOAL and Y-GOAL are varied within slew rate limits to accomplish sector scanning in a plane that can be tilted, panned, or rotated in any way consistent with angular excursion limits. Scan angle amplitudes and rates must be constrained by power dissipation limits to avoid overheating the AimServo transducer module. When displaying scan sector information, known lag characteristics between X-GOAL and Y-GOAL and true alignment response may be used to correct for proper positioning of features of the display. Alternatively, the demodulator outputs "X" and "Y"

Beam Generation and Alignment with Variable Focusing

In the variable focus embodiment of the invention, two-dimensional alignment and focusing of an ultrasound beam are achieved simultaneously by control of the translations and rotations of a single moving ultrasound reflector element, which is neutrally buoyed in ultrasound transmission fluid and magnetically servoed to desired orientations and axial locations, resulting in specified beam alignments and focus depths. FIGS. 9a through 9d show the electromagnetic and acoustic components of this embodiment built up by stages, not to show the sequence of manufacturing assembly, but simply for illustration.

Figure 9A:
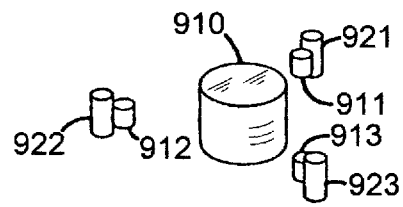
FIG. 9a illustrates details from FIG. 4, of the permanent magnets in a magnetic-levitation ultrasound beam alignment and focusing servo, while FIG. 9b adds vertical-axis position-servos and an ultrasound aiming and focusing mirror on the rotor magnet, FIG. 9c adds 2-axis rotation-servos.

First to go quickly through the assembly components, FIG. 9a shows the seven permanent magnets of the assembly. The central puck-shaped rotor magnet 910 is poled axially upward. The three inner perimeter magnets, 911, 912, and 913, are also poled upward, parallel to the poling of the center magnet. The three larger outer perimeter magnets, 921, 922, and 923, are poled axially downward. The function of the six magnets surrounding 910 is to stabilize the position of 910 laterally in the plane of the surrounding magnets and to stabilize the orientation of 910 for the poling axis to point up. With the proper orientation of 910, the effect of 911, 912, and 913, which are poled upward, parallel to 910, is to center 910, since the three surrounding magnets all repel 910 and tend to hold it centered. Axially, out of the plane of the holding magnets, 910 experiences a negative restoration from the positioning magnets, and this is overcome by servo control with vertical drive coils, as discussed below. With only inner-perimeter magnets 911, 912, and 913, the pole-up orientation of 910 is unstable, since the poling of 910 bucks the downward-directed center field resulting from 911, 912, and 913. The longer and stronger outer-perimeter magnets 921, 922, and 923 are poled axially downward and are strong enough to reverse the net field at the center of 910, causing a weak upward-pointing field vector. The magnetic field gradient of the outer-perimeter magnets tends to weaken the in-plane centering effect of the inner-perimeter magnets but to leave a weak net centering restoration. The technique for obtaining simultaneous positive in-plane centering and axis restoration as described is based on the fact that field gradients drop off more steeply than net field strengths as a function of distance from a perimeter magnet. The proportion of gradient centering effect to net-field orienting effect favors centering for nearer magnets and orienting for farther-away magnets. The arrangement illustrated, using larger or more powerful or more numerous magnets around an outer perimeter, in relation to smaller or less powerful or less numerous magnets around an inner perimeter, allows for net stabilization of in-plane position and orientation simultaneously. If orientation were unstable in the pole-up position and the magnet were to flip pole-down, then position would immediately become unstable as well, since the centering forces would be reversed. Hence, the passive centering described here works only for tilts of the center rotor magnet of less than 90° from nominal zero-tilt alignment.

Figure 9B:
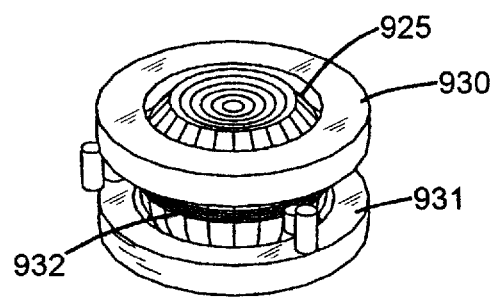
FIG. 9d illustrates in elevation section the completed assembly including ultrasound transducer, focus-correcting ultrasound window, and case.

In FIG. 9b, magnet 910 of FIG. 9a is not visible because it lies in the center of sphere 925 with symmetric dimples on the axially "up" and "down" ends. Only the "up" end shows in FIGS. 9b and 9c, but the cross-section in FIG. 9d shows the top and bottom concave dimples and the outline of magnet 910 in the center of dimpled sphere 925. This dimpled sphere is made of low-density material, e.g. polystyrene foam with a tough outer skin, and the geometric proportions and densities are balanced such that dimpled sphere 925 is nearly neutrally buoyant in surrounding ultrasound transmission fluid. Hence, the effects of gravity and translational accelerations of the housing around 925 are minimized by buoyancy, so that it is less difficult to keep 925 centered. From electromagnetic theory it can be shown that the negative or destabilizing position restoration force coefficients of 910 for vertical, or z-axis, displacements, is equal in magnitude to the sum of the positive or stabilizing position restoration force coefficients in x-axis and y-axis directions. If the negative z-axis restoration is too great, then excessive vertical drive current will be required to maintain a position above or below the unstable equilibrium point. If the negative restoration is made small in order to obtain acceptable position-drive power, then positive passive restoration in the x and y axis directions must be correspondingly small, making horizontal-plane position sensitive to gravitational influence as well as acceleration of the transducer housing. By approximating neutral buoyancy of the rotor in the ultrasound transmission fluid, pressure gradients in the fluid counteract both gravity and the effects of linear accelerations of the housing, keeping the rotor centered in the horizontal plane and minimizing interaction with vertical-axis position control circuitry.

Vertical position control is accomplished magnetically using drive coils 930 and 931 of FIG. 9b, in conjunction with passive position sense coil 932, drawn as a band of windings girdling the equator of dimpled sphere 925, and also shown in FIG. 9d as a winding cross-section sitting in a shallow depression in dimpled sphere 925, so that the surface is kept comparatively smooth at the equator. Winding 932 is electrically a closed loop, or shorted coil, having no external wiring connections. When magnet 910 is an electrical conductor (e.g., not ceramic), then this rotor magnet will modify the response of winding 932 to some extent. Vertical position drive is provided by causing oppositely-rotating currents in coils 930 and 931, so that a gradient in vertical field strength is generated in the vicinity of magnet 910 with the net field strength going to zero at a center position along the vertical axis of symmetry. Magnet 910 is driven vertically toward increasing coil field strength paralleling the poling of 910. For optimizing drive efficiency, coils 930 and 931 should be spaced approximately as Helmholtz Coils, i.e. with center-to-center spacing equal to coil radius, which maximizes the field gradient between the coils. For same-rotation currents in 930 and 931, the magnetic fields of the two coils reinforce at the center point and, for Helmholtz spacing of the coils, field strength is fairly constant in the vicinity of the on-axis center point. In addition to the opposite-rotating drive current established in the coil pair 930, 931, a same-rotation high-frequency current is established in the two coils, which induces a current in shorted coil 932. This current is used functionally much like the current in position-sense winding 523 or 623, as illustrated in FIG. 5c or FIG. 6. This current is relatively insensitive to vertical position changes of the coil within motion limits, since the coil spacing gives rise to a comparatively uniform vertical field through the coil. This current is reduced as the cosine of rotor tilt angle away from vertical as the sense coil axis moves away from alignment with the vertical drive coil-pair axis. When dimpled sphere 925 is displaced vertically from center position, the oscillating current induced in winding 932 induces an opposite-rotation current in coils 930 and 931. This current is readily distinguished from the same-rotation current used to excite the induced response. Coupling from the sense coil back to the drive coils is reduced as the cosine of off-axis tilt, and since the induced current is reduced by the same cosine factor, the detected opposite rotation current from the drive coils varies as the square of the tilt cosine angle multiplied, approximately, by vertical position. Hence, it will be seen that the position sense signal is slightly non-linear with respect to vertical position and is reduced in strength by rotor tilt. The control signals for setting vertical position are modified to take account of these characteristics. The servo loop for controlling z-axis rotor position is described below.

Figure 9C:
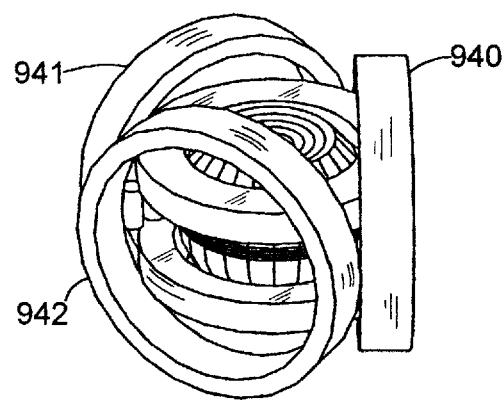

FIG. 9c illustrates the addition of rotation-drive coils 940, 941, and 942, which correspond functionally to coils 520, 521, and 522 of FIG. 5c, except that in this variable-focus embodiment, the planes of the three coils are vertical rather than tilted back. Horizontal-plane magnetic fields caused by currents in coils 940, 941, and 942 cause rotor 925 to tilt controllably with two-axis control. This tilt results in a coupling of the oscillating magnetic field from sense coil 932 (along with any effects of eddy currents in magnet 910) into an alignment that is resolved by circuitry as a net field in the (X,Y) plane, using decoding circuitry analogous to that explained in FIG. 8 and described below with reference to FIG. 12. Note that the tilt signal along a given axis, X or Y, will vary not simply as the direction-cosine of tilt in the X or Y direction, but rather as the direction-cosine of tilt multiplied by the cosine of net tilt, the latter reduction factor arising from the tilt-dependence of current induced in coil 932. Note that the direction-cosines of tilt, describing the projection of a unit vector paralleling the coil axis onto the (X,Y) plane, become simply the sine function of the off-axis tilt angle for tilt in either the X or Y direction, but not for intermediate directions. Hence, the direction cosines of tilt in X and Y directions should not be confused with the cosine of overall tilt angle.

FIG. 9d illustrates components of FIGS. 9a, 9b, and 9c in cross-section and with the addition of a housing and ultrasound components. Coils 930, 931, 932, and 940, magnets 910, 912, and 922, and dimpled sphere 925 all appear in the plane of the cross-section. Also shown are the walls of housing 950 and ultrasound window 960, which completes the housing and containment of ultrasound-transmitting fluid (e.g., water). As illustrated in the cross-section, the housing wall becomes thin at the extreme top and bottom surfaces of coil 940, where that and the other tilt-drive coils are captured by the indentations in the housing. It is seen that the coils also pass through cutouts in the edges of the ultrasound window. Vertical-drive coils 930 and 931 just touch the inside edges of tilt-drive coils 940, 941, and 942 and are secured at those points of contact. The perimeter pairs of permanent magnets, 911 with 921, 912 with 922, and 913 with 923, sit in the corners where the tilt-drive coils meet. In practice, the magnet pairs are encapsulated in non-magnetic material having a shape that is captured by the vertical-drive and tilt-drive coils and aids in retaining these coils in their proper positions. Note that ultrasound transmission fluid must be able to flow freely from the top of rotor 925 to the bottom, to allow for free vertical motion of the rotor. Rotor 925 itself is captured, and its excursions limited, by the inside surfaces of coils 930 and 931. As illustrated, these two coils are wound so that their inside surfaces are inclined conically to provide tangent contact with 925, rather than edge contact. In this preferred embodiment the coils are wound on a collapsible mandril, vacuum-impregnated with an epoxy, cured, removed from the mandril, and cleaned up to make structurally-sturdy components of the assembly. Wiring to the coils and ultrasound assembly is not shown in the drawings.

FIG. 10 illustrates the details of ultrasound window 960. Most of the material of the window, e.g., at 1001, is acoustically transparent at ultrasound frequencies and provides a positive refractive index to ultrasound waves exiting the ultrasound transmission fluid, implying that the speed of sound in the material is less than in the ultrasound fluid. Typically, the speed of sound in the material is also less than in the tissue to which the ultrasound window is coupled, e.g., by a coupling gel. In the ray-tracing diagrams of FIGS. 11a–11d, it is assumed that the speeds of sound in the ultrasound transmission fluid and in the tissue outside the window are equal and are 1.4 times greater than the speed of sound in the window material, implying a refractive index of 1.4 for the window with respect to either medium. Such a refractive index can be achieved with minimal boundary reflections by starting with silicone rubber, in which the speed of sound is less than in water or tissue and whose density is roughly the same as water or tissue. By adding a small amount of extremely dense material to the rubber before curing, e.g. very fine tungsten powder, the speed of sound in the rubber can be lowered slightly as the density of the rubber is increased. A concurrent increase in the bulk modulus of the rubber with loading partly offsets the reductions in sound speed in the material, while both the bulk modulus and density increases tend to raise the acoustic impedance. At an optimum loading, the acoustic impedance of the window material is raised to match that of the ultrasound transmission fluid, and, approximately, the acoustic impedance of the tissue to which the window will commonly be coupled. At this loading, the density of the window will be greater than for the ultrasound transmission fluid, and the speed of sound less, so that a positive index of refraction is achieved in the window without any reflection-generating difference in acoustic impedance. This no-reflection property of the lens has no direct counterpart in electromagnetic optics, for density and bulk modulus can both be controlled in an ultrasound window, whereas electromagnetic permeability and electrostatic permittivity cannot be controlled independently in a practical, transparent optical lens material.

In the center of lens 960 is an ultrasound transducer assembly consisting of transducer 1010, convex low-index lens component 1011, and concave high-index lens component 1012. In this preferred embodiment, lens component 1011 is the same liquid that is used for ultrasound transmission fluid below the lens, and lens component 1012 is the same material as the remainder of the window-lens assembly, as at 1001. Hence, window 1001 and lens component 1012 are formed as a single piece and transducer 1010 inserted into a well in the top of the piece, capturing fluid between 1010 and 1012 to form lens component 1011. The transducer itself consists of a flat piezoelectric disk in the middle of a sandwich. Going up from the disk, there is a high-acoustic-impedance damping layer, a low-density and low-impedance acoustic decoupling layer, and a tough outer-surface layer that forms part of the outer lens surface. The damping layer reduces transducer ringing, while the decoupling layer prevents transmission of ultrasound waves between the transducer and the medium directly above the ultrasound transducer, except via a path down through the lens and back up by reflection. Going down from the disk, there are two acoustic coupling layers of graduated acoustic impedance from the high impedance of the piezoelectric disk to the low impedance of lens component 1011. These layers, each roughly ¼ wavelength thick at the design center frequency of the transducer assembly, help couple acoustic energy through the large transition in acoustic impedance from the piezoelectric material to the lens. The details of ultrasound transducer design are well known in the art and are not subject to further discussion here. Fine wires, not shown, connecting electrically to the piezoelectric disk, are threaded through lens components 1011 and 1012 and affixed to the inner surface of lens 1001, leading to cable connections not shown and coupling ultrasound signals with the ultrasound electronics. Details of the ultrasound electronics are not given here since they are well known in the art and are not the subject of this disclosure.

The effect of lens components 1011 and 1012 is to de-focus ultrasound waves coming off the lower surface of transducer assembly 1010. Specifically, the transition from the relatively low-index medium of 1011 into concave high index element 1012 and back into the relatively low-index medium of the ultrasound transmission fluid accomplishes the defocusing. Converging spherical wavefronts arriving from the reflector-dimple surface of 925 are flattened going up through the lens to meet transducer 1010.

The size choice for the ultrasound transducer is constrained by ultrasound wavelength and by acceptable interference of the transducer with the beam traveling through the ultrasound window. The latter constraint is obvious: if the transducer occupies too large a fraction of the window aperture, its presence will interfere significantly with both outgoing and incoming ultrasound waves passing through the window. Since the transducer is far from a focal point for the main ultrasound beam going between the ultrasound dimple reflector and the imaged area, it does not affect any particular part of the image, but excessive transducer size, exceeding 10% to 20% of the window area, will cause significant interfering reflections and diffraction interference. At the minimum end of the size scale, if the transducer diameter becomes as small as two ultrasound wavelengths, then the assembly of lens components 1011 and 1012 becomes ineffective and beam diameter expands excessively by aperture diffraction. For outgoing waves, part of the ultrasound beam begins to miss the concave dimple reflector, and for incoming waves, much of the signal diffracts around the transducer assembly and passes out of the window unabsorbed. FIG. 10 illustrates an acceptable size compromise for the transducer and associated lens components.

FIGS. 11*a*–11*d* illustrate ultrasound optics of the variable-focus embodiment using ray-tracing diagrams. The details of the lens center, namely transducer 1010 and lens components 1011 and 1012, are not shown in these diagrams. Instead, a virtual point-source of ultrasound waves is illustrated roughly at the top surface of the lens assembly. The flat transducer and defocusing lens approximate an optical point source with a window allowing an included cone angle of roughly 60° i.e. 30° off-axis in any direction. The vertical drive coils, 930 and 931 of FIGS. 9*b*–9*d*, are included FIGS. 11*a*–11*d* in order to illustrate how far the rotor must move, in relation to geometric constraints, in order to traverse its focusing range. The cross-sections of the drive coils in the diagrams also provide a visual reference for rotor motions.

In FIG. 11*a*, the beam is represented by lines diverging from the source, hitting the concave dimple surface and reconverging above the window in the middle of gap 1101 in horizontal line segment 1102. The dimple in these diagrams and analysis is spherical, though the shape might advantageously be modified, taking into consideration the effects of lens 1001 on overall focus and optimizing the dimple and corrective lens shape together. Line segment 1102 represents the cross-section of an ultrasound target disk. Gap 1101 represents a hole in the center of a target, and the diameter of the hole represents roughly the diameter of the ultrasound beam under perfect focusing conditions, where focus resolution is limited by aperture diffraction effects. Most of the power of the ultrasound beam is concentrated inside this diameter. For an ultrasound frequency of 5 MHz and a diameter of 3 cm. for sphere 925, the aperture diameter represents roughly the diameter of the first circle of destructive interference in the diffraction pattern of an ultrasound beam arising from the diameter of the outermost intersections of the ray paths with the reflector dimple in 925. Raytracing is not entirely valid for analyzing optics where diffraction effects are so great, but as a rule, if all the rays in a diagram fall well within the aperture diameter illustrated at 1101, then focusing quality will approach diffraction limits and no further substantial improvement will be possible. The center-axis rays of the diagram represent two out-of-plane rays with angles from the ultrasound source corresponding to the in-plane rays illustrated. Observe in FIG. 11*a* that the center ray does not extend all the way down to the bottom-center of the reflector dimple, but stops at the level at which the inner of the two overlapping raytrace lines meets the upward-curving side of the reflector, out of the plane of the diagrammatic cross-section. These two ray traces are terminated in the target vicinity where they pass behind the plane of the diagram. Thus, the center-rays do not appear above the target. A slight separation of these rays can be observed in FIG. 11*d*, and in the other diagrams the rays are not separated to the resolution of the drawing.

Figure 11B:
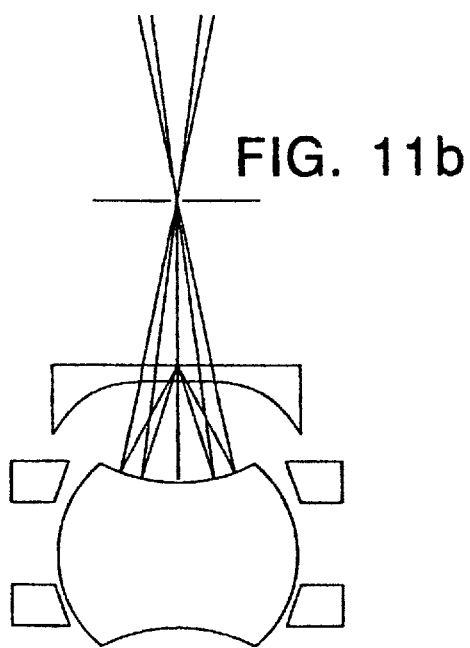

While FIG. 11a represents focusing an a nominal center-range depth, FIG. 11b represents focusing at a shallower depth. The target aperture is smaller for the shallower focus depth, consistent with diffraction limiting to fixed angular resolution. Observe that rotor 925 is displaced downward relative to coils 930 and 931, approaching its lower excursion limit. This lowers the ultrasound-reflecting dimple away from the ultrasound source and causes a closer focus. The rotor position is adjusted by the program that generates these diagrams so that convergence is optimized at the center of the target gap.

Figure 11C:
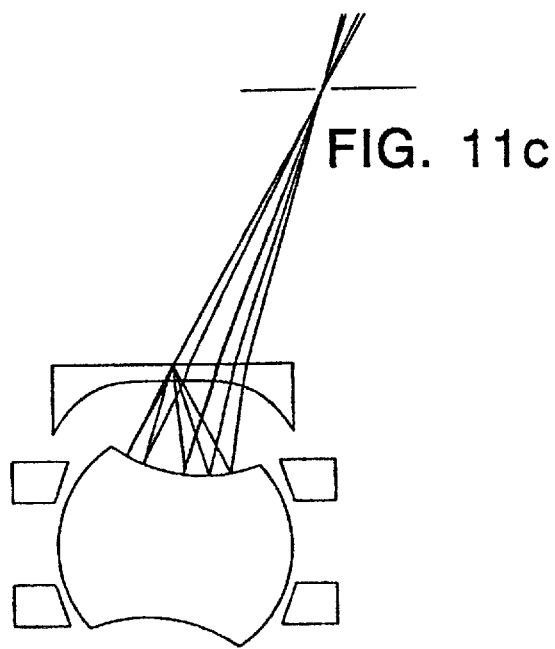

FIG. 11c illustrates optimum focusing when the target gap is kept in the same plane as in FIG. 11a and moved sideways to a 30° off-axis angle relative to the top center lens surface. To achieve this alignment, the dimpled sphere rotates through significantly less than half the nominal beam angle deflection, less than 8° for the deflection illustrated. Part of this ratio is explained by angle-doubling in a mirror: rotate a mirror 1° and a ray reflecting off its surface will be deflected by 2°. The remainder of the ratio is explained by tangential motion of the dimple reflector. Because the reflector is curved, a lateral translation of the surface causes a beam deflection. Since the mirror rotates about the sphere center rather than the point at the center of the mirror, a tangential component of motion of the mirror center is added to rotation of the mirror center in determining net angular deflection of the reflected beam. Hence, quite small angular rotor motions generate substantial beam-angle deflections.

Coil power requirements for aiming and focusing the ultrasound beam can be dominated by power to generate rotor translation, rather than angular deflection. Notice that when the rotor tilts to angle the beam sideways in FIG. 11c, it must also move axially downward to avoid movement of the focus to a greater depth. This rotor movement is seen by examining the position of the sphere surfaces in relation to the conical inner surfaces of coils 930 and 931. For rapid sector scanning through a large angle with optimum focus in a constant-depth plane, the coil power required to cause axial translations far exceeds the power required to generate the angular excursions. Since the focus-correcting axial displacements vary roughly as the square of angular displacement, at a constant scan frequency the power requirement for axial translation goes as the fourth power of scan angle, while the power for rotation goes as the square of scan angle. In optimizing the design for minimum power at large deflection angles, where axial deflection power far exceeds angular deflection power, the vertical drive coils have been placed inside the rotation drive coils to obtain the greatest field gradient for a given coil power. If the rotation drive coils were placed inside the vertical drive coils, then rotation-drive coupling would improve somewhat, but vertical-drive coupling would degrade by a much larger factor, since efficiency for producing a field gradient degrades more rapidly with increased coil size than efficiency for producing field strength.

Figure 11D:
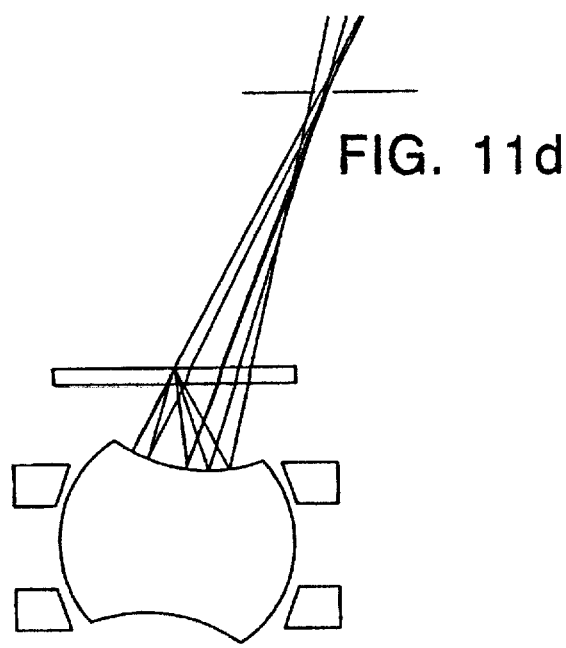

FIG. 11d illustrates optimum focusing on the same target as in FIG. 11c except without corrective curvature in lens 960. The rotor is positioned and rotated to minimize the mean-square error of intersection of the rays (four in-plane rays, two above-plane rays as illustrated, and the symmetric two behind-plane rays) with respect to the center of the target aperture. Note that the rotor is axially higher, as it would be for straight-ahead focusing as well, since the corrective lens here causes some divergent focusing that is overcome by placing the rotor a little lower than it would otherwise fall. The coma aberration error is quite significant in relation to the size of the diffraction pattern size, implying significant focus degradation. A coma-correcting lens appears to be very important to the quality of performance of the type of system being discussed, utilizing a concave rotating focusing mirror.

Alterations in mirror shape do not aid significantly in reducing off-axis focus aberrations, whereas a fixed lens works very well. In other raytrace studies, it has been shown that placing caps of high refractive index material over the sphere dimples to complete the sphere does not work well at all. The lens generated by this design supplements the mirror concavity for focusing, allowing a flatter mirror, but focus aberrations at off-axis angles are much worse. Completing the sphere by filling the dimples with material matching the ultrasound transmission fluid in refractive index has no focusing effect but has the advantage of minimizing fluid turbulence associated with sphere rotation, which can be advantageous where very smooth straight scan-paths are desired and where quick settling to a target angle is desired without disturbance from residual fluid turbulence. Filling the dimples increases sphere inertia somewhat, however, slowing responses at a given coil power level, so the merits of slewing speed versus smoothness of scan path and fast settling must be considered in an application context.

The curve illustrated in the lower surface of lens 960 is a pure fourth power law curve, scaled for optimum average focusing performance over a range of depths and angles. It is possible to add a small concave-up square-law component to the lens curve, making the lens thicker in the middle, thinnest at a radius off-center, and thinner at the edges. This shape is commonly observed in corrective lenses for light optics.

A number of effects influencing design optimization are noted here. For a given diameter and shape of the concave moving mirror, the indented ball can be comparatively large and spherical or small and relatively more flattened toward a puck-like shape, with the mirror surface area dominating over side surface area. For flatter shapes, the magnet will be smaller for a given mirror area to achieve buoyant balance, and fluid inertia associated with flow across the concave sections will be comparatively important, while for larger more nearly spherical shapes inertia of the magnet itself will become more significant. Since tangential motion of the concave mirror surface contributes significantly to the angular beam deflection caused by rotation, the larger more spherical shape will give a specified beam angle deflection with a smaller rotation of the magnet. For large-angle deflections, linear displacement to correct focus depth becomes a dominant component of power consumption. Translational inertia can be dominated by fluid inertia if there is little room for the fluid to get from the advancing to the receding side of the translating sphere. Note that the geometry shown allows fluid flow from the dimpled ends of rotor 925 outward past the outward-facing horizontal-plane surfaces of coils 930 and 931, around and through coils 940, 941, and 942, and with a vertical return flow path through the outer housing. An obvious alteration in the geometry of lens 960 would be to cut off the descending corners of the inside lens surface, where the surface never encounters the ultrasound beam, in order to increase the gap for fluid flow from the top of the rotor sphere 925 out over the top of coil 930.

Another design consideration is stray ultrasound paths. Ideally, ultrasound waves straying outside the design paths illustrated in FIGS. 11a–11d should be attenuated and absorbed. Ultrasound-absorbing coatings outside the target dimple reflector are desirable, e.g., on the convex surface of rotor 925, on the upper surface of coil 930, and on inner surfaces of housing 950.

It is seen that a performance model for design optimization needs to account for permanent fields, coil fields and their associated power dissipations, buoyant balance and appropriate proportioning of the rotating sphere and internal magnet, moving mass and rotational inertia, effective rotational fluid inertia caused by the mirror cavities, fluid inertia coupled to rotor translation, and beam angles and focus depths for given magnet positions and rotations.

Circuitry to Control Translation and Rotation

Figure 12:
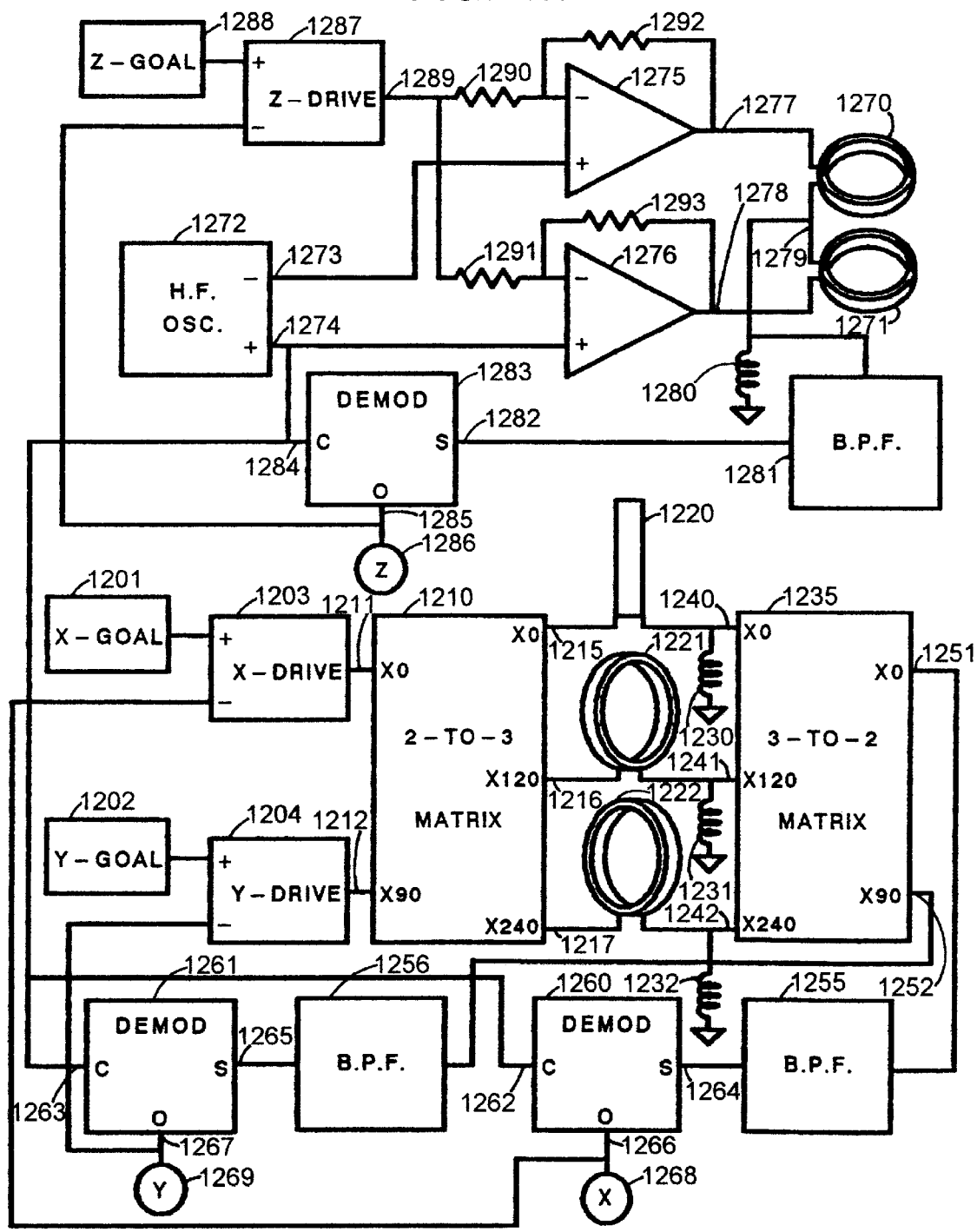
FIG. 12 illustrates circuitry for driving the linear and angular motions of the rotor of FIGS. 9c and 9d and for detecting the linear and angular position of that rotor.

There are many methods potentially applicable for measuring translations and rotations of rotor 925 and using those measures in a servo system, as discussed early in this disclosure. The preferred embodiment for variable focus and 2-axis variable alignment described here utilizes magnetic interactions with a high-frequency magnetic field and a shorted winding on the rotor, which appears to offer advantages of simplicity and economy. It is understood that the magnetics described above, and the circuit design described below, have been chosen as advantageous ways to achieve servo control, though not the only desirable approaches. An alternative method, utilizing motion-induced voltages in the drive coils, will be detailed later. Currently, we concentrate on the high-frequency carrier method with reference to FIG. 12. This approach closely parallels the approach described with reference to FIG. 6 except for the addition of vertical axis control and generation of the high-frequency sense magnetic field by induction in a shorted coil rather than by direct application of voltage to a coil on the rotor. We begin FIG. 12 with the circuitry that is directly analogous to circuitry in FIG. 6. Numbers 6xx of FIG. 6 are replaced with numbers 12xx for analogous circuitry in FIG. 12. By subtracting 600 from the diagram number, the following components of FIG. 12 are described by direct comparison with components of FIG. 6: 1201, 1202, 1203, 1204, 1210, 1211, 1212, 1215, 1216, 1217, 1220, 1221, 1222, 1230, 1231, 1232, 1235, 1240, 1241, 1242, 1251, 1252, 1255, 1256, 1260, 1261, 1262, 1263, 1264, 1265, 1266, 1267, 1268, and 1269. FIG. 7 applies to the detailed explanation of components 1203 and 1204 as before, and FIG. 8 applies to the matrixing of components 1210 and 1235 as before. Shorted coil 1223 corresponds to coil 932 (FIG. 9*b*) and is a functional cousin to coil 523 or 623 (FIG. 5 or 6), except that these directly-driven coils carry a current that is substantially independent of rotor orientation, whereas the induced current in coil 1223 is reduced with rotor tilt in proportion to the cosine of the overall tilt angle out of axial alignment. The reference carrier frequency is generated differently from FIG. 6, not by an autonomous high-frequency oscillator but by a resonant circuit involving the vertical drive coils, as is explained below. Because of differences in carrier generation, phase correction angles in the bandpass filters 1255 and 1256 may be somewhat different than in filters 655 and 656, though the filter functions serve the same purpose in either context—to bring the alignment sense signals into phase with the carrier for synchronous demodulation.

Examining further the aspects of FIG. 12 that differ from FIG. 6, first, the high-frequency carrier is generated by a tuned LCR circuit and an AGC feedback loop. Vertical drive coils 1270 and 1271 are driven, via outputs 1277 and 1278, from amplifiers 1275 and 1276, which respond with equal gain, polarity, and phase to the signal on output 1299 from AGC amp 1298. The coils are wired so that a signal from the AGC amp results in the same-rotation sense currents in 1270 and 1271, so that the magnetic fields reinforce at shorted sense winding 1223, setting up an induced current in that winding. The common mode current in coils 1270 and 1271 enters the transformer at 1280 via opposite ends of the primary winding, at 1292 and 1293. The currents from the ends meet at center tap 1274, generating virtually no net field in the transformer core since the currents in the two halves of the primary rotate in opposite senses for a common-mode drive signal. Thus, the transformer has little effect on common-mode current, adding only a little resistance and stray inductance. The summed currents on 1274 encounter the series combination of tuning capacitor 1294 and sense resistor 1295 to ground. The inductance of electrically-parallel coils 1270 and 1271 with the capacitance of 1294 results in a sharp resonant frequency-peaking at sense resistor 1295. The resulting current-sense signal from 1295 is connected via 1296 to noninverting fixed-gain amp 1279, whose output on 1297 feeds back to noninverting AGC amp 1298. The net gain around the loop just described is regenerative and maximal at the LC resonance frequency. The AGC amp includes an amplitude detector whose output is subtracted from a reference "target" level. The resulting level-error signal is integrated and otherwise phase compensated to compensate the AGC loop, and the resulting signal is applied to the gain-control input of a non-inverting voltage-controlled-gain amplifier from the input to the output of the AGC amp. The tuned-circuit loop establishes a low-distortion oscillation whose current amplitude is tightly regulated, despite changes in resonant Q-factor of coils 1270 and 1271 due to large displacements of the generally lower-Q coil 1223, whose close proximity to 1270 or 1271 typically lowers the gain of the regenerative loop compared to gain for a centered coil 1223. Low harmonic distortion is useful to avoid interference with ultrasound signal bands—a square-wave carrier drive signal would create serious problems. The tuned circuit approach also overcomes the reactive impedance of the drive coils at high frequency, so that a substantial carrier current can be established without demanding large power amplifier voltage drive capability. It is useful to have a well-regulated sense-current level in 1270 and 1271, since this level scales all the signals representing linear and angular position. Note that the amplitude detector in 1298 may be implemented as a synchronous demodulator like components 1260, 1261, and 1283 of the circuit. In the preferred embodiment, the three demodulators plus the AGC amplitude detector and voltage-controlled-gain amp all utilize the same integrated circuit type, LM1496, combined with op-amp sections for output buffering and filtering.

Note that the axis of sense coil 1223 is parallel to the poling axis of permanent magnet 1224, in the middle of 1223, so there is a symmetry between the carrier-frequency interactions with coil 1223 and the low-frequency magnetic drive interactions with magnet 1224. Thus, when a drive voltage to a coil results in actuation of a given mechanical degree-of-freedom, the high-frequency sense current appearing in the same coil will indicate the actuation achieved by the same degree-of-freedom. Hence, to drive vertical motion in magnet 1224, a differential mode signal is applied to coils 1270 and 1271, since the gains from the output of Z-DRIVE module 1287 on wire 1289 are of equal magnitude and opposite polarity at the non-inverting summing input of amp 1275 and the inverting summing input of amp 1276. The oppositely-rotating drive currents in the coils result in a z-axis magnetic field gradient that drives magnet 1224 up or down. The resulting shift in vertical position of sense coil 1223 causes an imbalance in the inductive coupling between 1223 and drive coils 1270 and 1271. As a result of the imbalance, the carrier-frequency signal induced in 1223 causes more current-change in the closer drive coil, less in the farther drive coil, so that there is an imbalance in the carrier currents on leads 1292 and 1293 to transformer

1280. This imbalance or differential-mode response current generates a net magnetic field in the transformer and a carrier-frequency response in the secondary winding, whose polarity and magnitude indicate the z-axis position of the rotor. Hence, differential-mode drive voltage results in differential-mode carrier current in the same coils. On the transformer secondary, lead 1290 is tied to ground reference while lead 1291 is connected to bandpass filter 1281, which provides appropriate gain and phase correction at the carrier frequency to drive synchronous demodulator 1283 via connection 1282 to the signal input, "S". The carrier for this demodulator at "C" is the amplified current-sense signal from the AGC loop, from amp 1279 on wire 1297, which also connects to the carrier inputs of demodulators 1260 and 1261 for sensing x and y tilt. The demodulated output "O" on 1285, labeled "Z" at 1286 for Z-axis position, is returned to the inverting input of the servo error detector and phase compensation circuit 1287, "Z-DRIVE", whose non-inverting input is provided from 1288, "Z-GOAL", the input value toward which detected position "Z" is driven. Circuit 1287 is the same kind of servo circuit as 1260 and 1261 and is described by FIG. 7 and accompanying text.

Since the current induced in coil 1223 is reduced as the cosine of the overall tilt angle, the sensitivity to tilt in signals "X" and "Y" at 1268 and 1269 will be correspondingly reduced. In fact, the maximum magnitude of the vector length SQRT(X2+Y2) for sensed X and Y is achieved at a net tilt of 450 away from the Z-axis. Further increases in tilt reduce the current in the sense coil to the extent that the overall demodulated tilt signal is reduced at higher angles. Similarly, z-axis position-sense gain is modulated by the cosine of overall tilt. These coordinate interactions must be taken into account in determining analog values for X-GOAL, Y-GOAL, and Z-GOAL, so that the actual desired beam alignment and focus are achieved. The geometric relationships involved are expressed fairly accurately by simple trigonometric expressions that can be implemented in a digital controller for the AimServo device.

Being an electromechanical system with inertia, the rotor will inevitably lag behind the position and orientation specified by the X, Y, and Z-GOAL inputs. Furthermore, because of changing couplings between actuation coils and the rotor magnet at large tilt angles, the dynamics of rotor response are nonlinear and somewhat complicated to model. The sense signals X, Y, and Z lag only slightly behind actual mechanical response, and the lag is quite predictable, arising from the linear characteristics of the filters used to suppress the carrier in the demodulator outputs. In mapping ultrasound signals to positions on a screen or positions in a computer-constructed 3-D projective image, the sense outputs from the servo are more useful than the control inputs. Small time-delay corrections and non-dynamic trigonometric corrections of the X, Y, and Z signals yield accurate representations of alignment and focus depth for each ultrasound pulse. Hence, in most imaging and mapping applications where the servo moves rapidly, good design will call for digital conversion of the analog sense signals as a part of mapping the locations in space associated with received ultrasound echoes and Doppler signals. The circuitry of FIG. 12 must be detailed with appropriate gains, controller transfer function breakpoints for integration and differentiation and band limiting, bandpass filter transfer functions and phase shifts at a chosen carrier frequency, and correct signal polarity connections in the demodulators to obtain negative rather than positive feedback. The same comments apply to the somewhat simpler circuitry of FIG. 6. In the preferred embodiments for fixed-focus and variable-focus ultrasound functions described, the goal signals are generated in a digital computer-controller which provides a user interface (keyboard plus mouse or joystick or track ball, control buttons, switches, knobs or slider pots, etc.), data-acquisition and display, generation of goal alignments, translation of the goal alignments into inputs for X-, Y-, and ZGOAL signals, and digital-to-analog conversion of those signals. The ultrasound decoding and display functions of the controller, including specialized ultrasound transmit/receive circuitry, gating, Doppler decoding, analog-to-digital conversion of position and rotation sense signals, video display, etc., follow existing designs except for utilization of X, Y, and Z sense signals (1268, 1269, and 1286) to determine actual alignments in dynamic situations. With the detailing described, readily accomplished by engineers skilled in the art and possibly with experimental optimization of gains and time constants, the controller circuits of FIG. 6 and FIG. 12 for 2-axis rotational alignment control and, in the case of FIG. 12, Z-axis translation control, will permit the successful aiming of an ultrasound beam for functions of scanning, tracking of targets, and the various imaging and mapping functions described elsewhere in this disclosure.

Control of Translation in X and Y

For the levitating rotor described above, control over translation in X and Y is by the passive centering force of permanent magnets. Strong passive centering in X and Y is inevitably accompanied by a strong negative centering in Z, to be countered by electromagnetic fields with continuous power consumption to hold the rotor far off-center. Neutral buoying of the rotor in ultrasound transmission fluid offsets gravitational pull and reduces the need for strong magnetic centering. There can be drawbacks to neutral buoyancy design, however, and active centering in X and Y may be desired.

Another potential need for active XY centering or damping arises from resonant instability in a rotor performing large periodic tilt rotations. Consider FIG. 9c where the top of the rotor is driven to tilt toward coil 940, on the right. The current in coil 940 will be twice the magnitude of the currents in either coil 941 or 942 (FIG. 8: for drive parallel to X0, weighting is +1 to X0 and −.5 to X120 and X240). The magnetic fluxes flowing through 941 and 942 converge in a "Y" and gain strength going to 940, reaching maximum strength somewhere between the center Z-axis and the center of coil 940. As the ball tilts to the right, the gradient in field strength from left to right interacts with the horizontal component of dipole field from the tilted rotor magnet, causing a translation force to the right. When the driving field reverses and the ball tilt reverses, leaning to the left, the ball is again drawn to the right, toward coil 940. A comparable effect is seen in the 120° and 240° directions and is absent at 60°, 180°, and 300°. The force is second order, varying as to the product of tilt angle and tilting-field strength, and therefore has frequency components at DC and at twice the tilt frequency. When the second harmonic of tilt frequency hits the natural resonance from the magnetic XY restoration force and the mass of the rotor (including entrained fluid mass), large wobbles can cause the rotor to bang against its confining coils. This wobble is reduced by a viscous ultrasound fluid, often an impractical fix. A software fix is to program the system to avoid large amplitude scanning at problem frequencies except in the unaffected 60° 180° and 300° tilt directions. One can use coils in fours, as symmetric opposing pairs, eliminating the wobble problem but sacrificing electromechanical efficiency by about 2.5 to 1. In an efficient three-way symmetry, a hardware solution is electromagnetic damping of XY translation, which can be achieved by passive means, more strongly by simple active feedback, and most strongly by full servo feedback.

For electromagnetic control approaches to XY translation, the three extra coils of FIG. 13 can be used. These horizontal-plane coils, drawn as non-circular stacks of photo-etched flat coils for compact packaging, lie between coils 930 and 931 and inside coils 940, 941, and 942 (FIGS. 9b and 9c). The magnetic field rising through the center of rotor magnet 910 or 1310 descends through horizontal-plane coils 1340, 1341, and 1342. When the magnet moves off-center, the flux in at least two of the horizontal-plane coils changes, implying an energy coupling that provides an opportunity for control.

The fully passive control approach is simply to short-circuit the horizontal plane coils. Horizontal motion of the rotor magnet will induce currents in the shorted coils, which will be dissipated by resistance, giving rise to electromagnetic damping comparable to that encountered in a voice coil speaker when its terminals are shorted or connected to a low-impedance amp. Electronically generated negative resistance is a way to increase this damping within limits: it is well known that when a magnet is lowered onto a superconducting surface, it will encounter what amounts to a spring restoration force, not an infinite damping. If velocity is measured independently, it is possible to achieve much greater feedback gain for tight control and quick response. As has been mentioned earlier, the beacon coordinates of magnet-winding interaction provide a natural framework in which to exert control, so that a controller consistently provides positive restoration and damping in all dimensions of motion, even as the coordinate map becomes extremely distorted. This subject leads to a description of the final embodiment of this disclosure.

Transcranial Doppler Ultrasound System

A 5-axis AimServo system for transcranial Doppler ultrasound is illustrated in plan view and section view in FIG. 13. The goal is to translate and rotate the rotor, aligning the beam until a thin spot or relatively ultrasound-transparent window is found in the skull. While this was once done entirely manually, remote control of a very compact package showed tremendous advantages, first as a means for remote manual control, and eventually as a means for automated tracking of Doppler targets while rejecting minor disturbances such as movement of the facial muscles, pulling on a sheet covering the transducer, etc. Continuous monitoring of central cerebral blood flow during surgery assures that the brain is getting oxygen and not being shut down by vascular spasm. Detection of floating plaques, heard in the audio Doppler display signal as an obvious rising whistle, became an unexpected and valuable bonus to cerebrovascular flow monitoring. Surgical techniques have improved in preventing the dislodging of plaques as a result of this form of monitoring. The AimServo system, used in this application, offers a tremendous increase in the utility of the entire system. But consider the design constraints.

A criterion for the transducer design was ability to extend the range of movement of the transducer-carrying rotor as far as possible toward one edge of the package. This edge is often advanced as far as possible from the eye dorsally toward the ear while maintaining the package in relatively flat contact, with ultrasound gel bridging to the patient's head across depressions. Good ultrasound windows are often found quite close to the ear. The implication for the design was that most of the coil space surrounding the rotor would have to be squeezed asymmetrically to one side, away from the ear, to maximize rotor travel toward the ear. A goal was for the overall weight of the transducer to be low enough that double-stick adhesive tape could hold the transducer package on the side of the head for extended periods. Too big a transducer would not fit a small face. Too little range of motion of the transducer would escalate the demand for very accurate initial placement on the head, partially defeating the advantage of the servo system. With the proportions illustrated in FIG. 13, it was necessary to design a hollow rotor that could be manufactured consistently within two or three percent of neutral buoyancy. A fixed-transducer rotor-mirror design was considered and rejected because the pulse-out/echo-return path became too long. An increased path calls for a lowering of pulse repetition rate, which in turn lowers the minimum frequency for aliasing, which in clinical practice unduly limits the maximum blood flow rate that can be measured without artifact. In the tether design, stiffness of the tether became a liability, like buoyancy imbalance: both require potentially excessive winding currents and lead to overheating or shutdown. It was initially assumed that there would be a beacon coil in the rotor, but this approach had problems. One was concern about interactions of the beacon magnetic field with metal near the sensor and with nearby electronic equipment, with interferences potentially traveling in both directions. Another liability was increased demand on the tether cable design. Finally, it was realized that the low cost of hall effect magnetic sensor integrated circuits with internal amplification could more than offset the costs of bandpassing, amplifying, and demodulating weak beacon carrier signals induced in the drive windings. The control mathematics was more difficult with the discrete sensors, entailing equations to infer, from multiple sensor readings, the position/orientation of the rotor, and then to compute the beacon coordinates of the rotor, i.e. the magnetic fluxes of the primary field magnet linking each coil at a given measurement cycle time. The conceptual equations that were expanded into computer code are given below.

The rotor assembly will now be described in greater detail, followed by a "rotor phantom" joystick assembly that is used for manual control of the servo target position.

As shown in FIG. 13, the sensor assembly consists of a rotor 1302 with an ultrasound transducer 1301 and a permanent magnet 1305; a spiral tether cable 1320 for carrying the ultrasound signal between the stator and transducer; a housing including an inner shell 1322, surrounding the rotor, to be filled with water or other fluid to buoy the rotor and transmit ultrasound to a rubber boot closing the open end of the shell (boot not shown); an outer housing 1324 in which the inner shell is placed off center to one side to allow rotor travel nearly to one edge of the housing; five drive windings, 1330 through 1334, to control the five coordinates of rotor motion, namely travel in x, y, and z, plus tilt out of axial alignment toward the x and y planes; and eight hall effect sensors, 1340 through 1347, which collectively over-determine the five coordinates of rotor position. The "extra" information from eight as opposed to five sensors is sufficient to solve for the perturbing effect of an external magnetic field on system measurements, e.g., the geomagnetic field, which is not insignificant even compared to the field of a nearby neodymium iron boron magnet a few diameters away: it is difficult to appreciate how rapidly the inverse cube-law field of a magnetic dipole weakens with distance as a 3000 gauss flux density at the surface of a magnet drops down to 5 to 20 gauss at a nearby sensor. In practice, the geomagnetic calibration involves parking the rotor in a shallow central depression (not shown) so that its position coordinates are known when the geomagnetic flux through the sensors is extracted, mathematically, from the sensor data.

Internal to the case, coax cable segment 1353 connects with spiral tether 1320 and with shell 1352, which encloses and shields the back of the ultrasound transducer crystal. This shell 1353 is of thin plastic and includes a thin outside coating of conductive paint that extends from the central coax shield radially outward, upward, and connects with the top conductive coating on the ultrasound transducer. A symmetry of current flow is maintained such that all ultrasound currents travel axially and radially in shell 1353, with currents breaking the radial symmetry. By this "coaxial" current flow design, all the magnetic flux lines generated by the ultrasound currents travel in closed tangential loops and are self-contained, communicating no radiation to the outside world. By this same symmetry, the ultrasound system is shielded against intruding external signals.

The rotor housing consists of thin shell halves 1350 and 1351 that slide together in telescoping fashion so that the total height of the rotor shell can be adjusted before adhesive or welding solvent is applied to bond the shell halves. The rotor parts can be weighed before joining and the overall height adjusted to achieve very nearly neutral buoyancy.

The relative effects of the different windings on rotor translation and rotation vary widely with rotor position, but for a centered rotor, the following approximate description characterized the primary roles of the individual windings. Axial coils 1330 and 1331 generate, at the center of 1334, gradients of vertical flux density, the flux becoming more concentrated going toward a current-carrying winding. When the rotor and its magnet are axially oriented, the magnet experiences horizontal translational forces toward greater flux density paralleling the magnet dipole vector or toward lesser flux density opposing the magnet dipole vector. The fields of 1330 and 1331 are roughly in geometric quadrature at the rotor center, giving relatively independent control of horizontal translation. Radial coils 1332 and 1333 generate fluxes at right angles to an axial magnetic moment vector, tending to tilt the magnet out of axial orientation into a horizontal direction in x and y. Again, the coils act approximately in quadrature for relatively independent control. Coil 1334 can enhance a y-axis in-plane field, or it can oppose the field produced collectively by 1332 and 1333. In the latter case, the effect is to generate an axial gradient of axial field strength, which generates a z-axis force in the rotor magnet. As the rotor moves off center and tilts, and as a consequence of the rotor magnet always being below the central plane of symmetry of the windings, the translational and torsional influences of the coils are strongly cross-coupled and highly dependent, in magnitude and direction, on the coordinates of the rotor.

The eight hall effect devices sense the component of B-field cutting through the thin dimension of the case. Thus, sensors 1340, 1343, and 1346, lying flat, sense axial field components, while 1341, 1344, and 1347 sense radial field components, and 1342 and 1345 sense tangential field components. Roughly speaking, five of the sensors correspond in sensitivity to the five coils: sensor 1340 to coil 1330, 1341 to 1332, 1343 to 1331, 1344 to 1333, and 1347 to 1334. These five sensors alone can uniquely determine magnet position and orientation throughout most—but not all—of the 5-dimensional control volume. There are singular points in the control volume where these five sensors do not resolve five independent rotor coordinates. A nonlinear coordinate mapping approximation given in the controller algorithm writeup below provides a non-singular mapping throughout the control region, and this mapping approximates the useful orthogonal coordinates of translation in x, y, and z, and tilt from z toward x and y.

Figure 14:
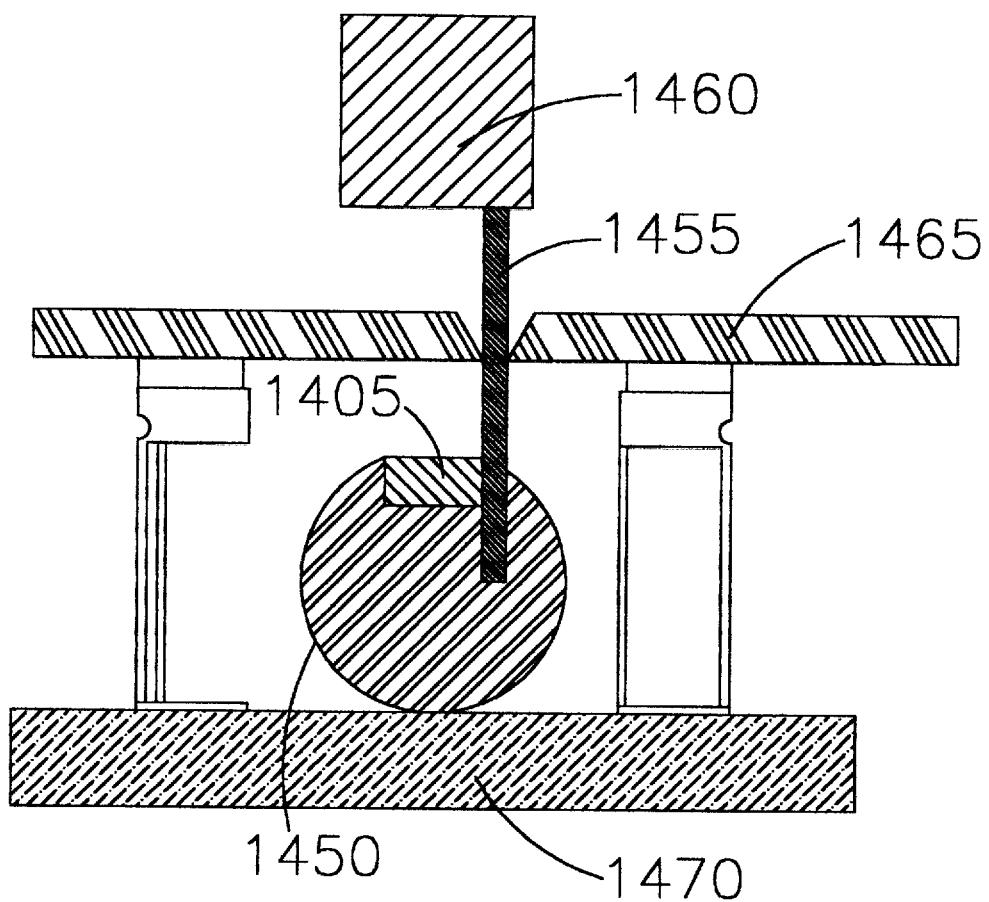
FIG. 14 illustrates in elevation section a rotating and translating joystick controller for manual control of the motions of the rotor shown in FIG. 13.

An important aspect of this particular AimServo system is its "phantom rotor" joystick assembly. As illustrated in FIG. 14, the "phantom" assembly is similar to the sensor assembly, containing an equivalent permanent field magnet 1405 in a rotor ball and hall effect sensors (not shown) in positions corresponding to the sensor assembly devices, to detect the coordinates of the magnet. In the phantom, however, there are no field windings and the rotor cavity is not filled with fluid. As drawn inverted relative to the components of FIG. 13, the rotor 1450 of FIG. 14 "looks" down rather than up, and the flat ultrasound transducer surface of FIG. 13 is replaced by the surface of a completed sphere rolling on the bottom of the housing in FIG. 14. Extending out of the ball is shaft 1455 extending into handle 1460. The shaft is off-center in the ball to clear the magnet on one side and, more importantly, to allow the ball to reach the full range of combined translation and rotation accessible to the sensor rotor. It is seen that without this shaft offset, one could not move the ball fully to the left and then rotate the handle as much as 30° further to the left to swing the ultrasound beam from off-center back across the central axis of the package. The shaft 1455 passes through a 60° conical hole in plate 1465, so that rotation of this shaft is limited to the same angular range accessible to the sensor rotor. Plate 1465 slides freely on top of the phantom housing shell, allowing a full range of rotation and translation of the phantom rotor, but if the joystick handle is released, friction is inclined to prevent the rotor from moving. When friction of the rolling ball 1450 prevents this ball from sliding, rocking the ball causes the axis of the ball (defined by the axis of the cylindrical field magnet in one end of the ball) to pivot about a point roughly at the surface of base block 1470. When the sensor rotor is caused to track the coordinates of the phantom rotor, then when the operator locates an ultrasound window in the skull, it is a very natural motion to cause the ultrasound beam to pivot about a point almost in the plane of the window, so that beam angular alignment is varied freely without losing the ultrasound transmission window. The mathematical method for causing the sensor rotor coordinates to match the joystick coordinates is now presented. This procedure illustrates the dynamic numerical calculation of beacon coordinates, as contrasted with more direct inductive measurement of the coordinates as described earlier. It further shows how these coordinates are used to achieve stable multidimensional control in a non-linear and variably cross-coupled system.

Position Location Algorithm & Driver Control Algorithm

The following procedure can be reduced to program code in an appropriate control microprocessor language, e.g., in "C", resulting in dynamic error correction to match the position and orientation of a levitated sensor rotor to the position and orientation of a "phantom" rotor, which consists of an assembly like the sensor but where the position and orientation of the rotor are set manually via a joystick, rather than by magnetic levitation.

The first part of the algorithm determines the position/orientation of the sensor rotor and of the phantom rotor, in the five coordinates of x position, y position, x tilt, y tilt, and z position. Computing the magnetic field components from a known rotor position/orientation at specified sensor positions and directional orientations is a relatively trivial mathematical problem. The inverse problem of inferring rotor position/orientation from sensor output measurements is more difficult, and is solved by a relatively fast-computing approximate numerical algorithm. Though the determination of position/orientation is inexact, the errors are the same for sensor and phantom coordinates, and driving the two position/orientation estimates to match does, in fact, drive the sensor rotor accurately to match the position/orientation of the phantom rotor.

The second part of the algorithm determines the voltage outputs to five drive coils that will drive the sensor coordinates to match those of the phantom. Toward that end, first the coordinates in position/orientation for the sensor and phantom are transformed into beacon coordinates, i.e., variables that are calculated to be proportional to the joules/ampere couplings between the primary field magnet (in either the sensor or the phantom) and each of the five corresponding drive coils. In this hardware design, there are no drive coils in the phantom assembly, but only hall effect field sensors to determine the coordinates of the phantom rotor. The question asked is, "What if the sensor rotor were positioned/oriented like the phantom rotor, with the same coordinates? In that case, what would be the beacon coordinates of the sensor rotor in its goal position?" This question is answered by computation, without need of coils in the phantom assembly. Given a set of target beacon coordinates for the rotor, derived from phantom measurements, the beacon coordinates for the sensor rotor at its present position are calculated. One then subtracts to get a coordinate error vector, in beacon coordinates, between the actual and target positions of the sensor rotor. One then wishes to generate, magnetically, a downhill energy slope from the actual sensor rotor position to the target sensor rotor position, downhill in the beacon coordinate system. This downhill slope is generated by applying currents, to the sensor drive windings, that are proportional to the five components of beacon coordinate error (obviously paying attention to the polarity required for a downhill energy slope.) At frequencies of concern for the embodiment under discussion, winding currents are proportional to and very nearly in phase with drive voltages, so for electronic convenience, voltage-output amplifiers are used to drive the windings.

The computed drive voltages are the proportional terms of the PID (Proportional, Integral, Derivative) control algorithm, as is familiar to engineers dealing with control of dynamic systems. Numerical differentiation results in time-derivative drive voltage terms that "anticipate" convergence and reduce rate of convergence to prevent overshoot. Numerical integration results in time-integral drive voltage terms that push steady-state errors to zero by effectively driving loop gain toward infinity for the steady state condition. Moving from overview to specifics, here is a description of the algorithm.

For either the sensor or the phantom, there are 8 hall effect sensors. Add a dummy 9th sensor, output=0, to give 3 groups of 3, used later.

The axial sensors, ax, lie flat in the plan-view of the assembly, pointing along +Z.

The radials, rd, are flat-face pointing radially out from center.

The two tangentials, tn, are flat-face pointing tangentially and angling toward +Y.

Looking down from top of board (standard view),
group=1@ −45 degrees (approx.), lower right, ax, rd , tn
group=2@ −135 degrees (approx.), lower left, ax, rd, tn
group=3@ +90 degrees, straight up, ax, rd, 0.0 (no tn sensor, output=0)

So our eight sensors+dummy, from the hardware, numbering from 0 to 8, are located (approx.):
0=−45 degree axial;
1=−45 degree radial;
2=−45 degree tangential;
3=−135 degree axial;
4=−135 degree radial;
5=−135 degree tangential
6=+90 degree axial;
7=+90 degree radial;
8=ZERO Conceptually divide these into 3 groups of 3, as in the form of a 3×3 matrix:

S[3,3]=S[group , (ax,rd,tn) ] for (axial, radial, tangential)

(Note that numbers in square brackets indicate numbers of turns in each successive dimension of a vector, a 2-dimensional matrix, or a 3-dimensional matrix. Terms lined up with comma separators between curved parentheses are vector components. Curved parentheses may, alternatively, indicate the parameter list of a function, e.g., f(x,y) for a function of arguments x and y. Usage should be inferred from context. The above matrix need not be created in computer code, but rather, calculations of terms may be written in expanded form.)

Assuming, for embodiment hardware, a nominal hall effect sensor sensitivity =2.341 mv/gauss and ±2.5 volts range (relative to center), we set gain=8 for sensors 0, 1, 2, 3, 4, 5 and gain=2 for sensors 6, 7.

The resulting output readings are in counts, from −2048 to +2047. We define floating point variables, gss, for "gauss" from these "count" outputs:
gss=15.338*count, for sensors 0, 1 , 2, 3, 4, 5
gss=3.834* count, for sensors 6, 7
gss=0, for "sensor" 8, the dummy These go into our 3×3 array S[3,3] in the following sequence (at least for conceptualization):

$$S[0, 0] = gss[0] \quad S[0, 1] = gss[1] \quad S[0, 2] = gss[2]$$

$$S[1, 0] = gss[3] \quad S[1, 1] = gss[4] \quad S[1, 2] = gss[5]$$

$$S[2, 0] = gss[6] \quad S[2, 1] = gss[7] \quad S[2, 2] = gss[8] = 0$$

For each sensor group, have a 3-vector, (ax,rd,tn) for sensor outputs in axial, radial, and tangential directions. This vector is a row from the S[3,3] matrix described just above.

Define output vector (R,THR,THT)(ax,rd,tn), for position estimate in R=Radial, THR=THeta-Radial, and THT=THeta-Tangent directions, i.e., a 3-vector output function of the 3-vector input:

Gauss · ref = 150,000. (a scaling constant)

Angle · fctn(ratio) = ratio − 0.6 * (ratio^3)

$R = (((2*ax)^2 + rd^2 + tn^2)/\text{Gauss} \cdot ref^2))^{(-1/6)}$ (this is in millimeter units)

$THR = -.5 * \text{Angle} \cdot fctn(rd/(2*ax))$ (this is in radian units)

$THT = \text{Angle} \cdot fctn(tn/(2*ax))$ (this is in radian units)

The vectors (R,THR,THT) from the three groups of hall effect devices are combined functionally to give a 4-vector, (x-defl,y-defl,x-tilt,y-tilt), in (millimeters, millimeters, degrees, degrees) up to a magnitude of about 6.5 millimeters maximum radius and 30 degrees maximum tilt magnitude. The computed deflections (x-defl,y-defl,x-tilt,y-tilt) are combined with the variables ax & rd to give vertical deflection z-defl. To define these transformations, we use three unit vectors representing the directions in which the three sensor groups are aligned, namely, −45 deg, −135 deg, and +90 deg. We also use three offset vectors representing the positions of these three sensor groups relative to the rotor center position. I will name these direction and offset vectors, give tables for their numerical values, and then give the equations that incorporate these vectors into a non-linear definition of position.

AXR[group] = (AXRx, AXRy) a two-dimensional unit radial direction vector assigned to each of 3 groups of sensors AXT[group] = (AXTx, AXTy) a two-dimensional unit tangent direction vector assigned to each of 3 groups of sensors XY[group] = (XYx, XYy) a two-dimensional location vector assigned to each of 3 groups of sensors

| | | |
|---|---|---|
| AXR[0] = (.707, −.707) | (1 unit at −45 degrees) | |
| AXR[1] = (−.707, .707) | (1 unit at −135 degrees) | |
| AXR[2] = (0, 1) | (1 unit at +90 degrees) | |
| AXT[0] = (.707,.707) | (1 unit at +45 degrees) | |
| AXT[1] = (−.707,.707) | (1 unit at +135 degrees) | |
| AXT[2] = (1,0) | (is unimportant since multiplied by zero for the dummy sensor) | |
| XY[0] = (13.59,−12.61) | (actual location, in millimeters, at roughly −45 degrees) | |
| XY[1] = (−13.59,−12.61) | (actual location, in millimeters, at roughly −135 degrees) | |
| XY[2] = (0,13.51) | (actual location, in millimeters, at +90 degrees) | |

(x-defl,y-defl)[group] = XY[group] − (AXR[group] * R[group])

where R[group] is from(R,THR,THT). This says that we start out at the location XY of the sensor group and travel a distance −R in the direction AXR. Since AXR points away from the center, −R times AXR points back from the sensor group location towards center, so that (x-defl,y-defl) can be zero for a centered rotor.

(x-tilt,y-tilt)[group]=57.3*(THR[group]*AXR[group]+ THT[group]* AXT[group])

Notice that THR[group] and THT[group] are scalar tilt quantities in radians. These are multiplied by the vectors AXR[group] and AXT[group], and the products summed, to give a vector tilt in radians. The scalar multiplier 57.3=180/pi scales the result to degree units, which are used in later calculations.

We now have a separate position & angle estimate, (x-defl,y-defl) & (x-tilt,y-tilt), from each group of sensors. These estimates are inaccurate, especially for the third group, which lacks tangential field information, but weighted averages of these estimates yield accurate location information. A few fudge factors are thrown in.

defl-x = SUM(x-defl) from (x-defl, y-defl) vector,
for SUM over group = 0 to 2 defl-y = SUM(y-defl) from (x-defl, y-defl) vector,
for SUM over group = 0 to 2 tilt-x = SUM(x-tilt) from (x-tilt, y-tilt) vector,
for SUM over group = 0 to 2

-continued tilt-y = SUM(y-tilt) from (x-tilt, 2y-tilt) vector,
for SUM over group = 0 to 2 net-defl-x = 0.92 * defl-x − 0.059 * tilt-x net-defl-y = 0.63 * defl-y − 0.029 * (3.35 + tilt-y)

net-tilt-x = 0.91 * tilt-x + 1.1 * defl-x net-tilt-y = 0.53 * (3.35 + tilt-y) + 0.73 * defl-y net-defl-z = −4700.0 * SUM(rd/(ax^4)) − 0.87

−0.17 * net-tilt-y      −0.0068 * (net-tilt-y^2)
                        −0.0066 * (net-tilt-x^2)
−0.10 * net-defl-y      −0.0236 * (net-defl-y^2)
−6.02

The SUM is over group=0 to 2. This final result is a position/orientation vector and is computed once for the phantom and once for the sensor. The very last additive constant, −6.02, represents an offset between the nominal magnet z and the z of the center-plane of the coils and is kept separate from the other additive term (−0.87) for organizational reasons.

NET-P=(net-defl-x, net-defl-y, net-tilt-x, net-tilt-y, net-defl-z) for phantom.

NET-S=(net-defl-x, net-defl-y, net-tilt-x, net-tilt-y, net-defl-z) for sensor.

For each of NET-P and NET-S we compute a coupling 5-vector for the 5 drive coils.

Define NET-*=NET-P or NET-S, to define a procedure to be repeated twice

CPL-*=(CPL1, CPL2, CPL3, CPL4, CPL5) for couplings to drive coils, Phantom or Sensor Coil numbering:

1 = lower right paisley-shape, + current = counter-clockwise or "up" by right hand rule 2 = lower left paisley-shape, + current = counter-clockwise or "up" by right-hand rule 3 = lower right pancake, + current rotates for radially-outward right-hand vector 4 = lower left pancake, + current rotates for radially-outward right-hand vector 5 = upper pancake, + current rotates for radially-outward right-hand vector AREA[4, 2, 3] = vector winding area, for first 4 coils, with 2 sub-areas each, area 3-vector (x, y, z)

XYZ[4, 2, 3] = locus of area centroid corresponding to AREA[4, 2, 3]

AREA#4[5, 3] = vector winding area of coil #4 numbering from zero, with 5 sub-areas, (x, y, z)

XYZ#4[5, 3] = locus of area centroid corresponding to AREA#4[5, 3]

Here are tabulations for the specific embodiment in question:

| | |
|---|---|
| AREA[0, 0, i] = (0, 0, 58.9) | area in square millimeters |
| XYZ[0, 0, i] = (7.0, −16.9, 0) | location in millimeters relative to center |
| AREA[0, 1, i] = (0, 0, 47.8) | |
| XYZ[0, 1, i] = (15.8, −7.1, 0) | |
| AREA[1, 0, i] = (0, 0, 58.9) | |

-continued

```
XYZ[1, 0, i] = (-7.0, -16.9, 0)
AREA[1, 1, i] = (0, 0, 47.8)
XYZ[1, 1, i] = (-15.8, -7.1, 0)
AREA[2, 0, i] = (52.8, -81.4, 0)    this and below are area magnitudes,
XYZ[2, 0, i] = (9.2, -14.2, 0)      radial directions
AREA[2, 1, i] = (90.6, -34.8, 0)
XYZ[2, 1, i] = (15.8, -6.1, 0)
AREA[3, 0, i] = (-52.8, -81.4, 0)
XYZ[3, 0, i] = (-9.2 , -14.2, 0)
AREA[3, 1, i] = (-90.6, -34.8, 0)
XYZ[3, 1, i] = (-15.8, -6.1, 0)
AREA#4[0, i] = (54.8, 23.9, 0)
XYZ#4[0, i] = (14.4, 6.3, 0)
AREA#4[1, i] = (59.4, 85.1, 0)
XYZ#4[1, i] = (9.0, 12.9, 0)
AREA#4[2, i] = (0.0, 103.79, 0)
XYZ#4[2, i] = (0.0, 15.7, 0)
AREA#4[3, i] = (-59.4, 85.1, 0)
XYZ#4[3, i] = (-9.0, 12.9, 0)
AREA#4[4, i] = (-54.8, 23.9, 0)
XYZ#4[4, i] = (-14.4, 6.3, 0)
```

Vector->Scalar Dot-Product subroutine for vectors A[3]= (Ax,Ay,Az), B[3]=(Bx, By, Bz):

DOT(A,B)=Ax*Bx+Ay*By+Az*Bz

Vector->Vector Cross-Product subroutine is defined (note ..xyzxyzxyz.. rotating order):

CROSS(A,B)=((Ay*Bz-Az*By), (Az*Bx-Ax*Bz), (Ax*By-Ay*Bx)

Vector dipole field of dipole moment vector M, radius vector RD, is defined:

B(M,RD)=((2*DOT(M,RD)×RD)+CROSS( CROSS(M, RD), RD))/DOT(RD,RD)^2.5

The two numerator terms are vectors, a scalar DOT product times vector RD, and a CROSS product whose arguments are a CROSS product and vector RD.

We get magnet locus and tilt for the phantom or the rotor:

NET-*=(net-defl-x, net-defl-y, net-tilt-x, net-tilt-y, net-defl-z)

M=( net-tilt-x/57.3, net-tilt-y/57.3, 1) is moment vector about 1 unit long, tilted from +Z RD[j,k,i]=XYZ[j,k,i]-( net-defl-x, net-defl-y, net-defl-z) for first 4 coils @ j=0 to 3, k=0 to 1

RD[4,k,i]=XYZ#4[k,i]-( net-defl-x, net-defl-y, net-defl-z) for last coil, k=0 to 4 where i=0 , 1 , 2 for the 3 vector components of XYZ. Defining a coupling factor for each entire coil j=0 to 4, with summations over k of length 2 for the first four coils and length 5 for the last coil:

CPL-*[j]=SUM.k[DOT( B(M,RD[j,k,i]), AREA[j,k,i])]

SUM.k is the summation over index k, the index for the subdivision of each coil into smaller component areas. Here, M is the moment vector defined from net-tilt-x and net-tilt-y a few lines above, RD[j,k,i] defined on the next two lines, the B(M,RD) function of these two arguments shown higher up, and the AREA[j,k,i] tabulated earlier. This is not a vector magnetic moment, but a vector parallel to the magnetic moment of the primary field magnet in the rotor, of magnitude varying from unity at zero tilt to slightly above unity for moderate tilt angles. Dimensions of the electromagnetic force problem, e.g., of magnetic moment, enter later into determination of the magnitudes of five drive coefficients, DRV.COEFF.

The DOT product sums over the three space directions i, and the SUM.k then sums over k, leaving the 5-vector CPL-*[j] corresponding to the 5 degrees of motion (defl-x, defl-y, tilt-x, tilt-y, defl-z) and used for the 5 coil currents.

The wild card "*" becomes P for Phantom and S for Sensor. The 5-vector DRIVE is then defined in terms of the differences between Phantom and Sensor CPL coil/rotor coupling factors, with a 5-vector DRV.COEFF[5] used to scale the drive signals:

DRV.COEFF[5] is 5-vector for scaling and balancing the magnitudes of the 5 drive coils DRV.COEFF is the proportional term in the PID (Proportional, Integral, Derivative) controller loop. The derivative & integral time constants of the PID multiply and divide (respectively) this proportional term.

DRIVE[j]=DRV.COEFF[5]*(CPL-S[j]-CPL-P[j]) in counts output, 4095 steps/20 volts

A working value:

DRV.COEFF[5]=( 340,000., 340,000., 340,000., 340,000., 340,000.)

Units for DRV.COEFF are step-millimeters. In steps described above, DRV.COEFF is multiplied by a coil area in mm ^2, then multiplied by a dipole field formula with an inverse-cube law in units mm^-3, yielding steps of digital/analog converter output. Geometric factors, the strength of the magnet, and the ratio (#turns/resistance) of the coils, enter the determination of DRV.COEFF.

t=0 is the present time sample, going back in time sample order for t=1, t =2, etc.

$PID[j]$ = DRIVE[$i$]($t$ = 0) +

CLAMP[$A$ * SUM(DRIVE[$j$]($t$ = all previous)] +

$B$ * (SUM(DRIVE[$j$]($t$ = 0 to $n$ - 1) - SUM(DRIVE[$j$]($t$ = $n$ to $2n$ - 1))

for A=IIR integral coeff, B=FIR derivative coeff, 2n=depth of derivative FIR filter.

Initial estimate: A=.02, B=1, n=4, based on approximately 250 laps/second of the control loop. CLAMP will limit magnitude buildup at ±50% of peak full scale, or a little more than ±1000 counts for a 12-bit digital/analog converter.

For this particular geometry, the mass and the rotational mass-moment of inertia are "equivalent" for the rotor, because the radius of gyration of the rotor mass along the tilt axis is approximately the same as the linear distance that extrapolates, from mid-position with the slope of the beacon coordinate function, to a 100% fractional change in beacon coordinate value. Therefore the algorithm as shown does not differentiate between the linear and rotation components of "distance" in coupling factor between the Phantom and the Sensor. (In a case of highly different time constants for different degrees of freedom, there can be separate steps, e.g., of first rotating, then translating, or first translating, then rotating, going from Phantom to Sensor coordinates, giving an intermediate coupling vector and separate differences for linear and torsional drive signal strengths, to receive different gain coefficients before going through linear and rotational PID algorithms whose outputs sum together to the 5 drive amplifiers.) The coils were designed to have roughly equivalent coupling strengths in driving their degrees of freedom, so the values for DRV.COEFF[5] are all the same in this example. The loop gain varies with rotor position, but within acceptable limits to allow stable convergence of sensor position/orientation to phantom position/orientation. (Otherwise, one would need to adjust the components of DRV.COEFF[5] adaptively according to the time-varying slope magnitudes of DRV.COEFF with respect to the five axes of translation/rotation.) The approximations in the above equations affect only speed and stability of convergence and not the final error between sensor and phantom position/orientation, provided that there is dynamic convergence and not runaway. The integration in the PID controller pushes differences in position/orientation between the sensor and phantom toward zero when the phantom is not moving. There is, of course, residual coordinate-mismatch error due to external magnetic fields, mismatch in field strengths of the primary field magnets in the phantom and the sensor, mismatch in sensor gains, offsets, and mechanical positioning, error associated with finite digital resolution of analog signals (both in and out), and dynamic "jitter" error due to circuit noise.

Although the present invention has been described with specific reference to detailed embodiments, it will be apparent to those skilled in the art that variations, modifications, and equivalents are possible without deviating from the basic scope of the invention.

I claim:

1. A levitation apparatus capable of providing a wide range of movement in three or more directions, the apparatus comprising:
   a) levitated rotor means capable of providing translational and two-axis tilt movement;
   b) stator means for inducing movement of said rotor means;
   c) sensing means for defining coordinates of said rotor means; and
   d) a servo-control means for controlling absolute direction of said rotor means in response to signals originating form said sensing means, said servo-control means providing signals to said stator means so as to provide movement of said rotor means.

2. The apparatus as claimed in claim 1 wherein said levitated rotor means includes an ultrasound means for directing an ultrasound beam.

3. The apparatus as claimed in claim 2 wherein said servo-control means provides rapid automated aiming and alignment of said ultrasound beam.

4. A method of ultrasound beam enhancement comprising the steps:
   a) levitating an ultrasound means;
   b) generating an ultrasound beam by way of said ultrasound means;
   c) controlling two-axis tilt movement [rotation] of said ultrasound beam with a servo controller; and
   d) controlling translation of said ultrasound beam with said servo controller.

5. An ultrasound-beam alignment servo-system comprising:
   a) a levitated rotor means capable of providing two-axis tilt movement, said rotor means including means for directing an ultrasound beam;
   b) stator means for inducing movement of said rotor means;
   c) sensing means for defining coordinates of said rotor means; and
   d) circuitry means for controlling said rotor means;
   wherein said sensing means relates position coordinates of said rotor means to said circuitry means so that said circuitry means controls said stator means and thereby controls movement of said rotor means and of said ultrasound beam.

6. The servo-system as claimed in claim 5 wherein said rotor means is a permanent magnet rotor.

7. The servo-system as claimed in claim 6 wherein:
   a) said position coordinates defined by said sensing means are beacon coordinates, wherein said beacon coordinates describe the position and the tilt of said permanent magnet rotor, wherein said beacon coordinates are defined proportionate to the energy-per-ampere-turn couplings between said permanent magnet rotor and multiple coils of said stator means; and
   b) associated with said beacon coordinates are target beacon coordinates defining a target position and orientation of said permanent magnet rotor;
   c) said circuitry means is responsive to differences between said beacon coordinates and said target beacon coordinates by causing currents in said multiple coils to vary as functions of said differences.

8. The servo-system as claimed in claim 7 wherein said means for directing said ultrasound beam is an ultrasound focusing mirror and said ultrasound focusing mirror is a part of said levitated body.

9. The servo-system as claimed in claim 8 wherein said stator means includes:
   a) a vertical-axis servo having at least one axial stator coil; and
   b) a two-axis rotation servo having two or more peripheral stator coils arranged around said levitated body.

10. The servo-system as claimed in claim 9 further comprising:
    a) a case means for containing said stator means and said rotor means;
    b) a focus-correcting ultrasound window located within a top section of said case; and
    c) an ultrasound transducer centrally located within said focus-correcting ultrasound window.

11. The servo-system as claimed in claim 10 wherein said levitated body is surrounded within said case by an ultrasound transmitting liquid.

12. The system as claimed in claim 7 wherein said permanent magnet rotor is a levitated body.

13. The system as claimed in claim 7 wherein:
    a) said sensing means includes a beacon coil means for creating an alternating-current magnetic field in said rotor;
    b) said beacon coil means includes at least one coil arranged concentric with a magnetic dipole center of said rotor and aligned to the magnetic moment of said dipole; and
    c) said beacon coordinates are determined by measurement of alternating-current voltages induced by said beacon coil in said multiple coils of said stator means.

14. The system as claimed in claim 13 wherein:
    a) said beacon coil means includes at least one loop of electrically conductive material defining a closed conductive path concentric with said magnetic dipole center and aligned to said magnetic moment; and
    b) said means for creating said alternating-current magnetic field in said rotor include means for generating an alternating-current magnetic field from said stator means, said field from said stator means inducing an alternating current in said closed conductive path, and said induced alternating current creating said alternating-current magnetic field in said rotor.

15. The system as claimed in claim 13 wherein;
    a) said permanent magnet rotor is electrically connected to said stator means by a tether cable; and,
    b) said beacon coil means is connected via said tether cable to said stator means for said creating said alternating-current magnetic field in said rotor.

16. The system as claimed in claim 7 wherein:

a) said sensing means includes multiple Hall-effect sensors for sensing vector components of the magnetic field of said permanent magnet rotor at selected locations and orientations; and b) outputs of said Hall-effect sensors are used to compute said beacon coordinates.

17. The servo-system as claimed in claim 5 wherein said means for directing said ultrasound beam is an ultrasound transducer, said ultrasound transducer is attached to said rotor means, and a tether electrically connects said stator means to said ultrasound transducer.

18. The servo-system as claimed in claim 17 wherein said stator means includes stator coils arranged around said rotor means.

19. The servo-system as claimed in claim 18 wherein said sensing means includes a beacon coil means for creating an alternating-current magnetic field in said rotor means.

20. The servo-system as claimed in claim 19 wherein said beacon coil means includes at least one coil arranged concentric with a magnetic dipole center of said rotor means and aligned to a magnetic moment of said magnetic dipole.

21. The servo-system as claimed in claim 20 wherein said ultrasound transducer is a fixed-focus ultrasound transducer.

22. The servo-system as claimed in claim 18 wherein said rotor means is a magnet rotor and wherein said sensing means includes beacon coil means for creating an alternating-current field in said rotor.

23. The servo-system as claimed in claim 22 wherein said sensing means further includes means for detecting the effect of said alternating-current field on said stator coils.

24. The servo-system as claimed in claim 5 wherein said rotor means is a magnet rotor and wherein said sensing means includes means for detecting a magnetic field of said magnet rotor so as to determine said coordinates of said magnet rotor.

25. The servo-system as claimed in claim 5 wherein said rotor means is surrounded by fluid and is levitated in said fluid by electromagnetic forces.

26. The servo-system as claimed in claim 25 wherein buoyant forces of said fluid exerted on said rotor means substantially reduce a magnitude of said electromagnetic forces required for levitation of said rotor means.

27. A servo system for controlling the coordinates of a transcranial Doppler ultrasound comprising:

a) a levitated rotor means within a housing and including means for directing said Doppler ultrasound;

b) means for inducing two-axis tilt movement of said rotor means;

c) sensing means for defining coordinates of said rotor means; and d) control means for controlling movement of said rotor means.

28. The servo system as claimed in claim 27 wherein said means for inducing movement of said rotor means is a stator means, said housing further comprising an inner shell for enclosing said rotor means and an outer shell for enclosing said stator means.

29. The servo system as claimed in claim 28 wherein said inner shell is positioned off center within said outer shell.

30. The servo system as claimed in claim 29 wherein said rotor means includes a permanent magnet.

31. The servo system as claimed in claim 30 wherein said stator means includes two or more stator coils arranged asymmetrically around said permanent magnet.

32. The servo system as claimed in claim 31 wherein said two or more stator coils are controlled by said control means so as to provide translational and said two-axis tilt movement to said permanent magnet.

33. The servo system as claimed in claim 32 wherein said sensing means includes means for detecting a magnetic field of said permanent magnet so as to determine coordinates of said rotor means.

34. The servo system as claimed in claim 33 wherein said sensing means includes a plurality of hall effect sensors.

35. The servo system as claimed in claim 34 wherein said means for directing said Doppler ultrasound is an ultrasound transducer.

36. The servo system as claimed in claim 35 wherein said rotor means is levitated by electromagnetic forces.

37. The servo system as claimed in claim 36 further comprising a fluid within said inner shell and surrounding said rotor means.

38. The servo system as claimed in claim 37 wherein buoyant forces of said fluid substantially reduce the magnitude of said electromagnetic forces required to levitate said rotor means.

39. The servo system as claimed in claim 27 wherein said means for inducing movement of said rotor means is a joystick coupled to said rotor means.

40. The servo system as claimed in claim 39 further comprising a slidable plate coupled to said housing, wherein said joystick includes a shaft extending through an opening of said plate and into an interior section of said housing.

41. The servo system as claimed in claim 27 wherein said means for inducing movement of said rotor means includes means for controlling translational movement of said rotor means.

42. The servo system as claimed in claim 41 wherein said means for inducing movement of said rotor means further includes means for controlling rotational movement of said rotor means.

* * * * *

UNITED STATES PATENT AND TRADEMARK OFFICE
Certificate

Patent No. 5,844,140                                                      Patented: December 1, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Joseph B. Seale, Gorham, ME; and Gary E. Bergstrom, Chagria Falls, OH.

Signed and Sealed this Sixteenth Day of February, 1999.

HEZRON E. WILLIAMS
*SPE*
Art Unit 2856